United States Patent
Horvath et al.

(10) Patent No.: US 10,940,040 B2
(45) Date of Patent: Mar. 9, 2021

(54) INTRAOCULAR SHUNT PLACEMENT

(71) Applicant: AqueSys, Inc., Aliso Viejo, CA (US)

(72) Inventors: Christopher Horvath, Mission Viejo, CA (US); Laszlo O. Romoda, San Clemente, CA (US)

(73) Assignee: AQUESYS, INC., Aliso Viejo, CA (US)

(*) Notice: Subject to any disclaimer, the term of this patent is extended or adjusted under 35 U.S.C. 154(b) by 219 days.

(21) Appl. No.: 15/882,984

(22) Filed: Jan. 29, 2018

(65) Prior Publication Data
US 2018/0147089 A1 May 31, 2018

Related U.S. Application Data

(60) Division of application No. 14/843,887, filed on Sep. 2, 2015, now Pat. No. 9,877,866, which is a continuation of application No. 14/191,340, filed on Feb. 26, 2014, now Pat. No. 9,192,516, which is a continuation of application No. 12/946,653, filed on Nov. 15, 2010, now Pat. No. 8,663,303.

(51) Int. Cl.
*A61F 2/958* (2013.01)
*A61F 9/007* (2006.01)

(52) U.S. Cl.
CPC .............................. *A61F 9/00781* (2013.01)

(58) Field of Classification Search
CPC ...... A61F 2/06; A61F 2/16; A61F 2/95; A61F 2/954; A61F 2/958; A61F 2/966; A61F 2/962; A61F 9/007; A61F 9/00781; A61F 9/00736
See application file for complete search history.

(56) References Cited

U.S. PATENT DOCUMENTS

| | | |
|---|---|---|
| 3,654,932 A | 4/1972 | Newkirk |
| 3,788,327 A | 1/1974 | Donowitz et al. |
| 3,960,150 A | 6/1976 | Hussain et al. |
| 4,090,530 A | 5/1978 | Lange |
| 4,402,308 A | 9/1983 | Scott |
| 4,562,463 A | 12/1985 | Lipton |
| 4,583,117 A | 4/1986 | Lipton et al. |
| 4,613,329 A | 9/1986 | Bodicky |
| 4,700,692 A | 10/1987 | Baumgartner |
| 4,722,724 A | 2/1988 | Schocket |
| 4,730,613 A | 3/1988 | Gordy |
| 4,744,362 A | 5/1988 | Grundler |
| 4,750,901 A | 6/1988 | Molteno |

(Continued)

FOREIGN PATENT DOCUMENTS

| | | |
|---|---|---|
| CN | 1402625 | 3/2003 |
| CN | 1909859 | 2/2007 |

(Continued)

OTHER PUBLICATIONS

Pediatric Surgery, vol. e, 7th edition, published on Feb. 14, 2012 to Coran et al., pp. 1673-1697.

(Continued)

*Primary Examiner* — Vi X Nguyen
(74) *Attorney, Agent, or Firm* — Nathan S. Smith; Sujohn Das; Morgan, Lewis & Bockius LLP

(57) ABSTRACT

Methods are provided for using an intraocular shunt deployment device to deploy an intraocular shunt from the device and into an eye.

19 Claims, 18 Drawing Sheets

(56) References Cited

U.S. PATENT DOCUMENTS

| | | |
|---|---|---|
| 4,787,885 A | 11/1988 | Binder |
| 4,804,382 A | 2/1989 | Turina et al. |
| 4,820,626 A | 4/1989 | Williams et al. |
| 4,826,478 A | 5/1989 | Schocket |
| 4,836,201 A | 6/1989 | Patton et al. |
| 4,848,340 A | 7/1989 | Bille et al. |
| 4,863,457 A | 9/1989 | Lee |
| 4,902,292 A | 2/1990 | Joseph |
| 4,908,024 A | 3/1990 | Py |
| 4,911,161 A | 3/1990 | Schechter |
| 4,915,684 A | 4/1990 | MacKeen et al. |
| 4,934,363 A | 6/1990 | Smith et al. |
| 4,936,825 A | 6/1990 | Ungerleider |
| 4,946,436 A | 8/1990 | Smith |
| 4,968,296 A | 11/1990 | Ritch et al. |
| 4,978,352 A | 12/1990 | Fedorov et al. |
| 5,041,081 A | 8/1991 | Odrich |
| 5,057,098 A | 10/1991 | Zelman |
| 5,071,408 A | 12/1991 | Ahmed |
| 5,092,837 A | 3/1992 | Ritch et al. |
| 5,098,426 A | 3/1992 | Sklar et al. |
| 5,098,443 A | 3/1992 | Parel et al. |
| 5,162,641 A | 11/1992 | Fountain |
| 5,167,645 A | 12/1992 | Castillo |
| 5,178,604 A | 1/1993 | Baerveldt et al. |
| 5,180,362 A | 1/1993 | Worst |
| 5,201,750 A | 4/1993 | Hocherl et al. |
| 5,207,660 A | 5/1993 | Lincoff |
| 5,273,530 A | 12/1993 | Del Cerro |
| 5,275,622 A | 1/1994 | Lazarus |
| 5,290,295 A | 3/1994 | Querals et al. |
| 5,300,020 A | 4/1994 | L'Esperance, Jr. |
| 5,333,619 A | 8/1994 | Burgio |
| 5,338,291 A | 8/1994 | Speckman et al. |
| 5,342,370 A | 8/1994 | Simon et al. |
| 5,351,678 A | 10/1994 | Clayton |
| 5,360,339 A | 11/1994 | Rosenberg |
| 5,368,015 A | 11/1994 | Wilk |
| 5,370,607 A | 12/1994 | Memmen |
| 5,399,951 A | 3/1995 | Lavallee et al. |
| 5,410,638 A | 4/1995 | Colgate et al. |
| 5,443,505 A | 8/1995 | Wong et al. |
| 5,476,445 A | 12/1995 | Baerveldt et al. |
| 5,516,522 A | 5/1996 | Peyman et al. |
| 5,520,631 A | 5/1996 | Nordquist et al. |
| 5,558,629 A | 9/1996 | Baerveldt et al. |
| 5,558,630 A | 9/1996 | Fisher |
| 5,601,094 A | 2/1997 | Reiss |
| 5,656,026 A | 8/1997 | Joseph |
| 5,665,093 A | 9/1997 | Atkins et al. |
| 5,665,114 A | 9/1997 | Weadock et al. |
| 5,670,161 A | 9/1997 | Healy et al. |
| 5,688,562 A | 11/1997 | Hsiung |
| 5,695,474 A | 12/1997 | Daugherty |
| 5,704,907 A | 1/1998 | Nordquist et al. |
| 5,707,376 A | 1/1998 | Kavteladze et al. |
| 5,722,948 A | 3/1998 | Gross |
| 5,763,491 A | 6/1998 | Brandt et al. |
| 5,868,697 A | 2/1999 | Richter et al. |
| 5,908,449 A | 6/1999 | Bruchman et al. |
| 5,932,299 A | 8/1999 | Katoot |
| 5,938,583 A | 8/1999 | Grimm |
| 5,964,747 A | 10/1999 | Eaton et al. |
| 6,007,511 A | 12/1999 | Prywes |
| 6,007,578 A | 12/1999 | Schachar |
| 6,050,970 A | 4/2000 | Baerveldt |
| 6,086,543 A | 7/2000 | Anderson et al. |
| 6,102,045 A | 8/2000 | Nordquist et al. |
| 6,146,366 A | 11/2000 | Schachar |
| 6,159,218 A | 12/2000 | Aramant et al. |
| 6,165,210 A | 12/2000 | Lau et al. |
| 6,203,513 B1 | 3/2001 | Yaron et al. |
| 6,228,023 B1 | 5/2001 | Zaslavsky et al. |
| 6,228,873 B1 | 5/2001 | Brandt et al. |
| 6,231,546 B1 | 5/2001 | Milo |
| 6,261,256 B1 | 7/2001 | Ahmed |
| 6,264,665 B1 | 7/2001 | Yu et al. |
| 6,280,468 B1 | 8/2001 | Schachar |
| 6,413,540 B1 | 7/2002 | Yaacobi |
| 6,450,937 B1 | 9/2002 | Mercereau et al. |
| 6,471,666 B1 | 10/2002 | Odrich |
| 6,483,930 B1 | 11/2002 | Musgrave et al. |
| 6,514,238 B1 | 2/2003 | Hughes |
| 6,524,275 B1 | 2/2003 | Lynch et al. |
| 6,533,768 B1 | 3/2003 | Hill |
| 6,544,249 B1 | 4/2003 | Yu et al. |
| 6,558,342 B1 | 5/2003 | Yaron et al. |
| 6,595,945 B2 | 7/2003 | Brown |
| 6,638,239 B1 | 10/2003 | Bergheim et al. |
| 6,699,210 B2 | 3/2004 | Williams et al. |
| 6,726,664 B2 | 4/2004 | Yaron et al. |
| D490,152 S | 5/2004 | Myall et al. |
| 6,736,791 B1 | 5/2004 | Tu et al. |
| 6,752,753 B1 | 6/2004 | Hoskins et al. |
| 6,881,198 B2 | 4/2005 | Brown |
| 6,936,053 B1 | 8/2005 | Weiss |
| 6,939,298 B2 | 9/2005 | Brown et al. |
| 7,008,396 B1 | 3/2006 | Straub |
| 7,037,335 B2 | 5/2006 | Freeman et al. |
| 7,041,077 B2 | 5/2006 | Shields |
| 7,094,225 B2 | 8/2006 | Tu et al. |
| 7,118,547 B2 | 10/2006 | Dahan |
| 7,135,009 B2 | 11/2006 | Tu et al. |
| 7,163,543 B2 | 1/2007 | Smedley et al. |
| 7,186,232 B1 | 3/2007 | Smedley et al. |
| 7,207,980 B2 | 4/2007 | Christian et al. |
| 7,291,125 B2 | 11/2007 | Coroneo |
| 7,331,984 B2 | 2/2008 | Tu et al. |
| 7,431,709 B2 | 10/2008 | Pinchuk et al. |
| 7,431,710 B2 | 10/2008 | Tu et al. |
| 7,458,953 B2 | 12/2008 | Peyman |
| 7,488,303 B1 | 2/2009 | Haffner et al. |
| 7,594,899 B2 | 9/2009 | Pinchuk et al. |
| 7,625,384 B2 | 12/2009 | Eriksson et al. |
| 7,658,729 B2 | 2/2010 | Hull |
| 7,708,711 B2 | 5/2010 | Tu et al. |
| 7,722,549 B2 | 5/2010 | Nakao |
| 7,837,644 B2 | 11/2010 | Pinchuk et al. |
| 7,867,186 B2 | 1/2011 | Haffner et al. |
| 7,892,282 B2 | 2/2011 | Shepherd |
| 8,109,896 B2 | 2/2012 | Nissan et al. |
| 8,267,882 B2 | 9/2012 | Euteneuer et al. |
| 8,277,437 B2 | 10/2012 | Saal et al. |
| 8,308,701 B2 | 11/2012 | Horvath et al. |
| 8,313,454 B2 | 11/2012 | Yaron et al. |
| 8,337,393 B2 | 12/2012 | Silverstrini et al. |
| 8,337,509 B2 | 12/2012 | Schieber et al. |
| 8,377,122 B2 | 2/2013 | Silvestrini et al. |
| 8,425,449 B2 | 4/2013 | Wardle et al. |
| 8,444,589 B2 | 5/2013 | Silvestrini |
| 8,486,000 B2 | 7/2013 | Coroneo |
| 8,506,515 B2 | 8/2013 | Burns et al. |
| 8,512,404 B2 | 8/2013 | Frion et al. |
| 8,529,492 B2 | 9/2013 | Clauson et al. |
| 8,535,333 B2 | 9/2013 | de Juan, Jr. et al. |
| 8,545,430 B2 | 10/2013 | Silvestrini |
| 8,585,629 B2 | 11/2013 | Grabner et al. |
| 8,597,301 B2 | 12/2013 | Mitchell |
| 8,608,632 B1 | 12/2013 | Brigatti et al. |
| 8,663,303 B2 | 3/2014 | Horvath et al. |
| 8,721,702 B2 | 5/2014 | Romoda et al. |
| 8,758,290 B2 | 6/2014 | Horvath et al. |
| 8,765,210 B2 | 7/2014 | Romoda et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,974,511 B2 | 3/2015 | Horvath et al. |
| 9,017,276 B2 | 4/2015 | Horvath et al. |
| 9,044,301 B1 | 6/2015 | Pinchuk et al. |
| 9,095,411 B2 | 8/2015 | Horvath et al. |
| 9,095,413 B2 | 8/2015 | Romoda et al. |
| 9,192,516 B2 | 11/2015 | Horvath et al. |

(56) References Cited

U.S. PATENT DOCUMENTS

| | | |
|---|---|---|
| 9,271,869 B2 | 3/2016 | Horvath et al. |
| 9,283,116 B2 | 3/2016 | Romoda et al. |
| 9,326,891 B2 | 5/2016 | Horvath et al. |
| 9,393,153 B2 | 7/2016 | Horvath et al. |
| 2001/0025150 A1 | 9/2001 | de Juan et al. |
| 2001/0056254 A1 | 12/2001 | Cragg et al. |
| 2002/0087149 A1 | 7/2002 | McCary |
| 2002/0099434 A1 | 7/2002 | Buscemi et al. |
| 2002/0133168 A1 | 9/2002 | Smedley et al. |
| 2003/0015203 A1 | 1/2003 | Makower et al. |
| 2003/0050574 A1 | 3/2003 | Krueger |
| 2003/0060752 A1 | 3/2003 | Bergheim et al. |
| 2003/0093084 A1 | 5/2003 | Nissan et al. |
| 2003/0097053 A1 | 5/2003 | Itoh |
| 2003/0187383 A1 | 10/2003 | Weber et al. |
| 2003/0236483 A1 | 12/2003 | Ren |
| 2003/0236484 A1 | 12/2003 | Lynch et al. |
| 2004/0077987 A1 | 4/2004 | Rapacki et al. |
| 2004/0147870 A1 | 7/2004 | Burns et al. |
| 2004/0199130 A1 | 10/2004 | Chornenky et al. |
| 2004/0210209 A1 | 10/2004 | Yeung et al. |
| 2004/0215133 A1 | 10/2004 | Weber et al. |
| 2004/0216749 A1 | 11/2004 | Tu |
| 2004/0236343 A1 | 11/2004 | Taylor et al. |
| 2004/0254521 A1 | 12/2004 | Simon |
| 2004/0260227 A1 | 12/2004 | Lisk et al. |
| 2005/0049578 A1 | 3/2005 | Tu et al. |
| 2005/0101967 A1 | 5/2005 | Weber et al. |
| 2005/0143363 A1 | 6/2005 | De Juan et al. |
| 2005/0246023 A1 | 11/2005 | Yeung |
| 2005/0267398 A1 | 12/2005 | Protopsaltis et al. |
| 2005/0271704 A1 | 12/2005 | Tu et al. |
| 2005/0277864 A1 | 12/2005 | Haffner et al. |
| 2006/0052721 A1 | 3/2006 | Dunker et al. |
| 2006/0064112 A1 | 3/2006 | Perez |
| 2006/0106370 A1 | 5/2006 | Baerveldt et al. |
| 2006/0116625 A1 | 6/2006 | Renati et al. |
| 2006/0149194 A1 | 7/2006 | Conston et al. |
| 2006/0155238 A1 | 7/2006 | Shields |
| 2006/0173397 A1 | 8/2006 | Tu et al. |
| 2006/0173446 A1 | 8/2006 | Dacquay et al. |
| 2006/0200113 A1 | 9/2006 | Haffner et al. |
| 2006/0241411 A1 | 10/2006 | Field et al. |
| 2007/0093783 A1 | 4/2007 | Kugler et al. |
| 2007/0118065 A1 | 5/2007 | Pinchuk et al. |
| 2007/0141116 A1 | 6/2007 | Pinchuk et al. |
| 2007/0172903 A1 | 7/2007 | Toner et al. |
| 2007/0191863 A1 | 8/2007 | De Juan et al. |
| 2007/0263172 A1 | 11/2007 | Mura |
| 2007/0293872 A1 | 12/2007 | Peyman |
| 2008/0015633 A1 | 1/2008 | Abbott et al. |
| 2008/0027304 A1 | 1/2008 | Pardo et al. |
| 2008/0057106 A1 | 3/2008 | Erickson et al. |
| 2008/0108933 A1* | 5/2008 | Yu .................. A61M 27/008 604/8 |
| 2008/0147001 A1 | 6/2008 | Al-Marashi et al. |
| 2008/0181929 A1 | 7/2008 | Robinson et al. |
| 2008/0249467 A1 | 10/2008 | Burnett et al. |
| 2008/0281277 A1 | 11/2008 | Thyzel |
| 2008/0312661 A1 | 12/2008 | Downer et al. |
| 2009/0036818 A1 | 2/2009 | Grahn et al. |
| 2009/0043321 A1 | 2/2009 | Conston et al. |
| 2009/0124973 A1 | 5/2009 | D'Agostino et al. |
| 2009/0182421 A1 | 7/2009 | Silvestrini et al. |
| 2009/0209910 A1 | 8/2009 | Kugler et al. |
| 2009/0216106 A1 | 8/2009 | Takii |
| 2009/0264813 A1 | 10/2009 | Chang |
| 2009/0270890 A1 | 10/2009 | Robinson et al. |
| 2009/0281520 A1 | 11/2009 | Highley et al. |
| 2009/0287136 A1 | 11/2009 | Castillejos |
| 2010/0004581 A1 | 1/2010 | Brigatti et al. |
| 2010/0063478 A1 | 3/2010 | Selkee |
| 2010/0063512 A1 | 3/2010 | Braga |
| 2010/0098772 A1 | 4/2010 | Robinson et al. |
| 2010/0100104 A1 | 4/2010 | Yu et al. |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0134759 A1 | 6/2010 | Silvestrini et al. |
| 2010/0137981 A1 | 6/2010 | Silvestrini et al. |
| 2010/0173866 A1 | 7/2010 | Hee et al. |
| 2010/0191103 A1 | 7/2010 | Stamper et al. |
| 2010/0249691 A1 | 9/2010 | Van Der Mooren et al. |
| 2010/0328606 A1 | 12/2010 | Peyman |
| 2011/0009874 A1 | 1/2011 | Wardle et al. |
| 2011/0046536 A1 | 2/2011 | Stegmann et al. |
| 2011/0098627 A1 | 4/2011 | Wilcox |
| 2011/0105990 A1 | 5/2011 | Silvestrini |
| 2011/0118745 A1 | 5/2011 | Yu et al. |
| 2011/0118835 A1 | 5/2011 | Silvestrini et al. |
| 2011/0230890 A1 | 9/2011 | Thyzel |
| 2011/0234976 A1 | 9/2011 | Kocaoglu et al. |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123434 A1 | 5/2012 | Grabner et al. |
| 2012/0165720 A1 | 6/2012 | Horvath et al. |
| 2012/0165933 A1 | 6/2012 | Haffner et al. |
| 2012/0197175 A1 | 8/2012 | Horvath et al. |
| 2012/0226150 A1 | 9/2012 | Balicki et al. |
| 2012/0310137 A1 | 12/2012 | Silvestrini |
| 2013/0158462 A1 | 6/2013 | Wardle et al. |
| 2013/0184631 A1 | 7/2013 | Pinchuk |
| 2013/0211314 A1 | 8/2013 | Boey et al. |
| 2013/0237958 A1 | 9/2013 | Arrigo |
| 2013/0245573 A1 | 9/2013 | de Juan, Jr. et al. |
| 2013/0253528 A1 | 9/2013 | Haffner et al. |
| 2013/0281817 A1 | 10/2013 | Schaller et al. |
| 2013/0281908 A1 | 10/2013 | Schaller et al. |
| 2013/0345515 A1 | 12/2013 | Fitzmaaurice |
| 2014/0066833 A1 | 3/2014 | Yaron et al. |
| 2014/0081195 A1 | 3/2014 | Clauson et al. |
| 2014/0135916 A1 | 5/2014 | Clauson et al. |
| 2014/0213958 A1 | 7/2014 | Clauson et al. |
| 2014/0236066 A1 | 8/2014 | Horvath et al. |
| 2014/0243730 A1 | 8/2014 | Horvath |
| 2014/0275923 A1 | 9/2014 | Haffner et al. |
| 2014/0276332 A1 | 9/2014 | Grimaldi et al. |
| 2014/0277349 A1 | 9/2014 | Vad |
| 2014/0303544 A1 | 10/2014 | Haffner et al. |
| 2014/0323995 A1 | 10/2014 | Clauson et al. |
| 2014/0371651 A1 | 12/2014 | Pinchuk |
| 2015/0005689 A1 | 1/2015 | Horvath et al. |
| 2015/0011926 A1 | 1/2015 | Reitsamer et al. |
| 2015/0038893 A1 | 2/2015 | Haffner et al. |
| 2015/0133946 A1 | 5/2015 | Horvath et al. |
| 2015/0265469 A1 | 9/2015 | Bhandari et al. |
| 2015/0290035 A1 | 10/2015 | Horvath et al. |
| 2015/0374545 A1 | 12/2015 | Horvath et al. |
| 2016/0135993 A1 | 5/2016 | Horvath et al. |
| 2016/0135994 A1 | 5/2016 | Romoda et al. |
| 2016/0158063 A1 | 6/2016 | Romoda et al. |
| 2018/0199797 A1 | 7/2018 | London |
| 2019/0030285 A1 | 1/2019 | Prabhu |
| 2019/0054272 A1 | 2/2019 | Tal |
| 2019/0069770 A1 | 3/2019 | Bourget |
| 2019/0290314 A1 | 9/2019 | Gemer |
| 2020/0046213 A1 | 2/2020 | Bendory |
| 2020/0054353 A1 | 2/2020 | Yun |

FOREIGN PATENT DOCUMENTS

| | | |
|---|---|---|
| CN | 101677823 | 3/2010 |
| CN | 102170840 | 8/2011 |
| CN | 102481171 | 5/2012 |
| CN | 102510746 | 6/2012 |
| GB | 2 296 663 A | 7/1996 |
| JP | 2009-523540 | 6/2009 |
| JP | 2012-527318 | 11/2012 |
| JP | 2014-500758 | 1/2014 |
| RU | 2313315 C2 | 12/2007 |
| RU | 2482822 | 5/2013 |
| WO | WO-98/23237 A1 | 6/1998 |
| WO | WO-00/056255 A1 | 9/2000 |

(56) References Cited

FOREIGN PATENT DOCUMENTS

| WO | WO-2002/74052 A2 | 9/2002 |
| WO | WO-2007/087061 A2 | 8/2007 |
| WO | WO-2008/005873 A2 | 1/2008 |
| WO | WO 2010/003011 | 1/2010 |
| WO | WO 2014/150292 | 9/2014 |
| WO | WO 2016/023942 | 2/2016 |
| WO | WO 2017/184881 | 10/2017 |

OTHER PUBLICATIONS

Quere, "Fluid Coating on a Fiber," Annu. Rev. Fluid Mech. 1999, 31:347-84.

\* cited by examiner

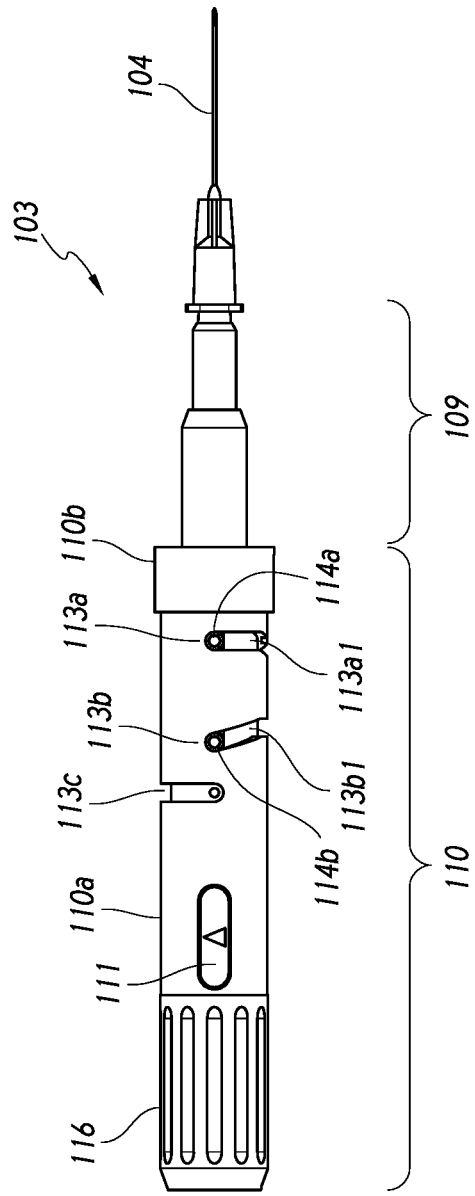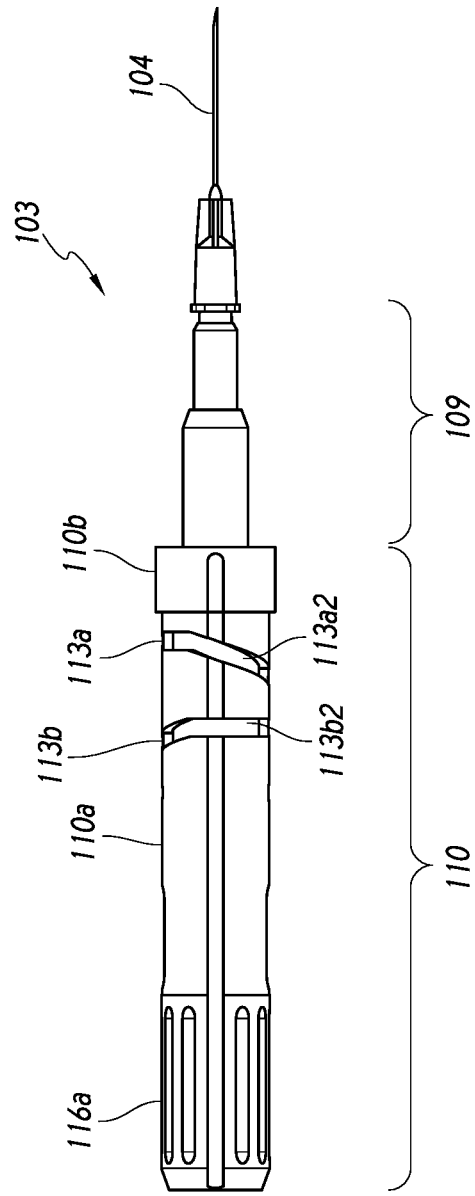
FIG. 3A
FIG. 3B

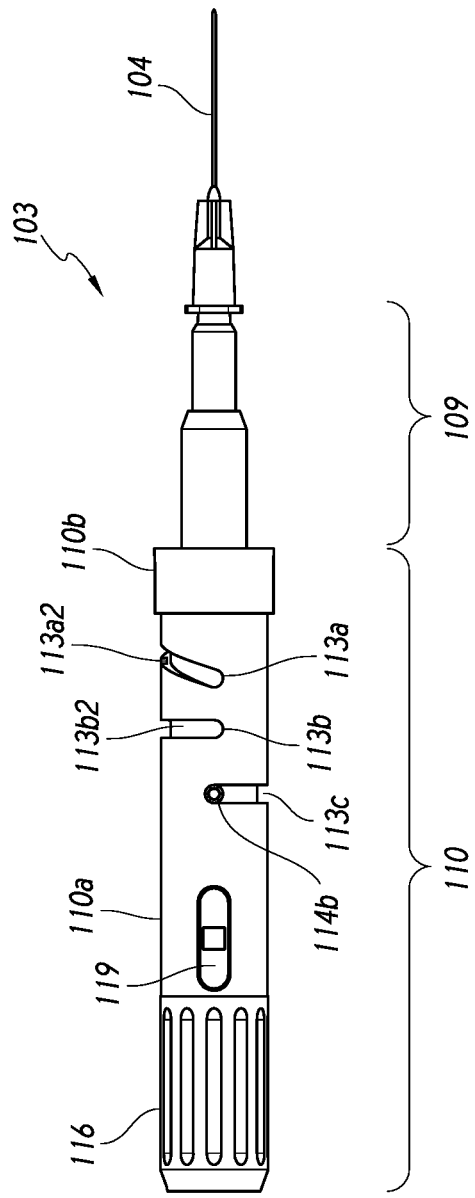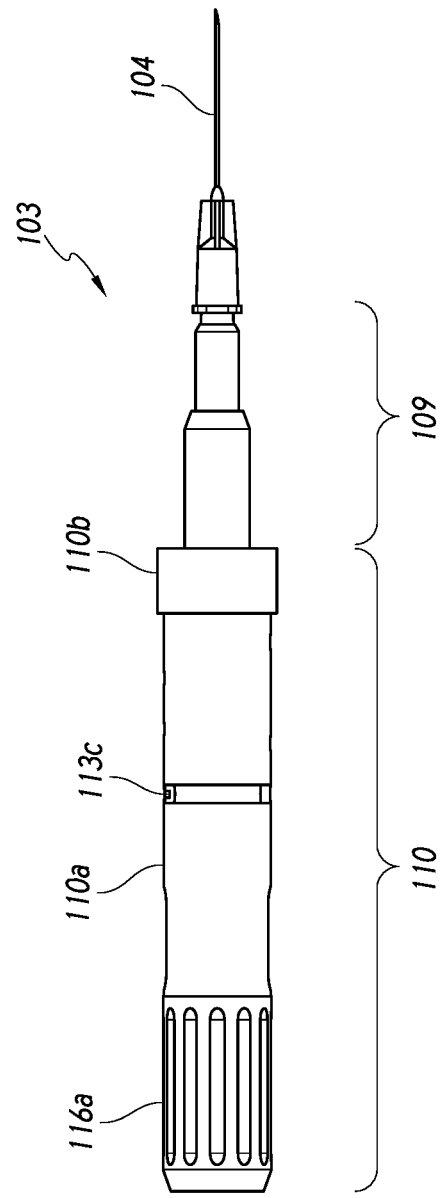

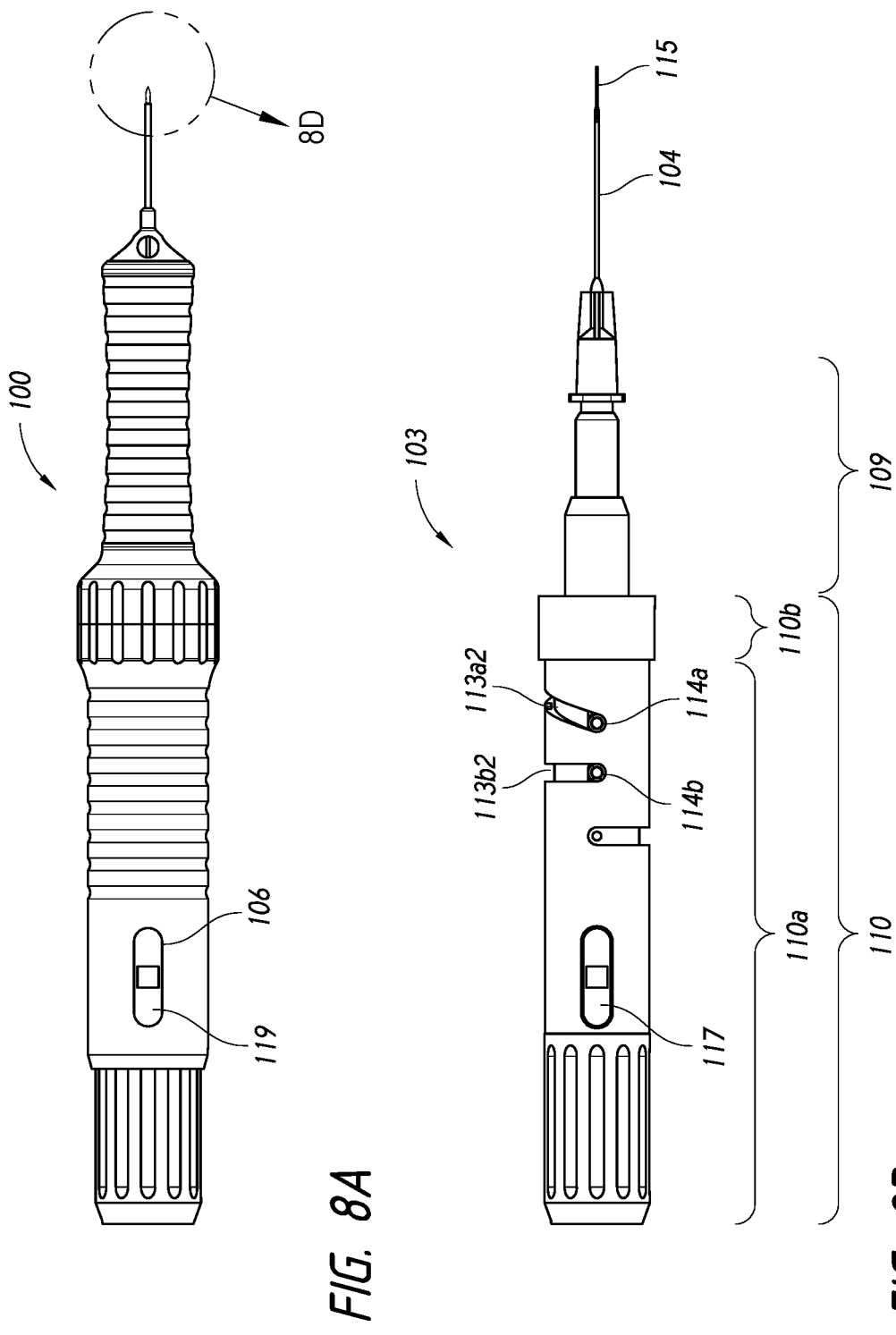

INTRAOCULAR SHUNT PLACEMENT

CROSS-REFERENCE TO RELATED APPLICATIONS

This application is a divisional of U.S. patent application Ser. No. 14/843,887, filed on Sep. 2, 2015, which is a continuation of U.S. patent application Ser. No. 14/191,340, filed on Feb. 26, 2014, now U.S. Pat. No. 9,192,516, which is a continuation of U.S. patent application Ser. No. 12/946,653, filed on Nov. 15, 2010, now U.S. Pat. No. 8,663,303, the entireties of each of which is incorporated herein by reference.

BACKGROUND

Field of the Invention

The invention generally relates to methods for using an intraocular shunt deployment device to deploy an intraocular shunt from the device and into an eye.

Description of the Related Art

Glaucoma is a disease of the eye that affects millions of people. Glaucoma is associated with an increase in intraocular pressure resulting either from a failure of a drainage system of an eye to adequately remove aqueous humor from an anterior chamber of the eye or overproduction of aqueous humor by a ciliary body in the eye. Build-up of aqueous humor and resulting intraocular pressure may result in irreversible damage to the optic nerve and the retina, which may lead to irreversible retinal damage and blindness.

Glaucoma may be treated by surgical intervention that involves placing a shunt in the eye to result in production of fluid flow pathways between the anterior chamber and various structures of the eye involved in aqueous humor drainage (e.g., Schlemm's canal, the sclera, or the subconjunctival space). Such fluid flow pathways allow for aqueous humor to exit the anterior chamber. Generally, the surgical intervention to implant the shunt involves inserting into the eye a deployment device that holds an intraocular shunt, and deploying the shunt within the eye. A deployment device holding the shunt enters the eye through a cornea (ab interno approach), and is advanced across the anterior chamber. The deployment device is advanced through the sclera until a distal portion of the device is in proximity to a drainage structure of the eye. The shunt is then deployed from the deployment device, producing a conduit between the anterior chamber and various structures of the eye involved in aqueous humor drainage (e.g., Schlemm's canal, the sclera, or the subconjunctival space). See for example, Prywes (U.S. Pat. No. 6,007,511).

A problem associated with such surgical interventions is ensuring that placement of the shunt does not change during deployment of the shunt from the deployment device. Deployment devices that are used to place the shunt in the eye generally rely on multiple moving components in order to deploy the shunt. Movement of the components of the deployment device shifts the position of the deployment device within the eye during the deployment process, and thus shifts the position of the shunt as it is being deployed. Such movement leads to improper placement of the shunt within the eye.

SUMMARY

The invention generally relates to deployment devices that are designed to minimize movement of the device during deployment of an intraocular shunt from the device, thereby ensuring proper placement of the shunt within the eye.

In certain aspects, deployment devices of the invention include a housing, a deployment mechanism at least partially disposed within the housing, and a hollow shaft coupled to the deployment mechanism, in which the shaft is configured to hold an intraocular shunt. With such devices, rotation of the deployment mechanism results in deployment of the shunt. Such rotational movement is translated into axial movement for deploying the shunt from the device. By utilizing rotational movement for the deployment mechanism, axial movement of the deployment device is minimized, ensuring proper placement of the shunt within the eye.

Other aspects of the invention provide devices for deploying an intraocular shunt including a housing, a deployment mechanism at least partially disposed within the housing, in which the deployment mechanism includes a two stage system, and a hollow shaft coupled to the deployment mechanism, in which the shaft is configured to hold an intraocular shunt.

Another aspect of the invention includes devices for deploying an intraocular shunt including a housing, a deployment mechanism at least partially disposed within the housing, and a hollow shaft coupled inside the housing to the deployment mechanism, wherein the shaft is configured to hold an intraocular shunt, in which the device includes an insertion configuration and a deployment configuration and the deployment configuration includes a proximal portion of the shaft being at least partially retracted to within the housing. In certain embodiments, the insertion configuration includes a distal portion of the shaft being disposed within the housing and a proximal portion of the shaft extending beyond the housing.

In certain embodiments, the shaft is configured to at least partially retract to within the housing. However, it will be appreciated that the shaft may fully retract to within the housing.

In certain embodiments, the device further includes the intraocular shunt. The shunt may be completely disposed within the hollow shaft of the device. Alternatively, the shunt is partially disposed within the hollow shaft of the device.

The deployment mechanism may include a two stage system. In such embodiments, the first stage is a pusher component and the second stage is a retraction component. In this embodiment, rotation of the deployment mechanism sequentially engages the pusher component and then the retraction component. The pusher component pushes the shunt to partially deploy the shunt from within the shaft, and the retraction component retracts the shaft from around the shunt, thereby deploying the shunt. In certain embodiments, the deployment mechanism may additionally include at least one member that limits axial movement of the shaft.

The hollow shaft of the deployment device may include a beveled distal end. An exemplary hollow shaft is a needle. Devices of the invention may be completely automated, partially automated, or completely manual. Devices of the invention may be connected to larger robotic systems or may be used as stand-alone handheld deployment devices. In particular embodiments, the device is a handheld device.

Devices of the invention may include an indicator that provides feedback to an operator as to the state of the deployment mechanism. The indicator may be any type of indicator known in the art, for example a visual indicator, an audio indicator, or a tactile indicator. In certain embodiments, the indicator is a visual indicator.

Aspects of the invention also include methods for deploying an intraocular shunt within an eye. These methods involve using devices described herein to deploy an intraocular shunt from the device within the eye. Generally, deploying the shunt results in a flow path from an anterior chamber of the eye to an area of lower pressure. Exemplary areas of lower pressure include intra-Tenon's space, the subconjunctival space, the episcleral vein, the suprachoroidal space, and Schlemm's canal. In certain embodiments, the area of lower pressure is the subarachnoid space.

Any of a variety of methods known in the art may be used to insert devices of the invention into an eye. In certain embodiments, devices of the invention may be inserted into the eye using an ab externo approach (entering through the conjunctiva) or an ab interno approach (entering through the cornea).

BRIEF DESCRIPTION OF THE DRAWINGS

FIGS. 3A-3D are schematics showing different enlarged views of the deployment mechanism of the deployment device.

FIG. 8A shows a schematic of the deployment device after deployment of the shunt from the device.

FIG. 8B show a schematic of the deployment mechanism at the end of the second stage of deployment of the shunt from the deployment device.

DETAILED DESCRIPTION

Figure 1:
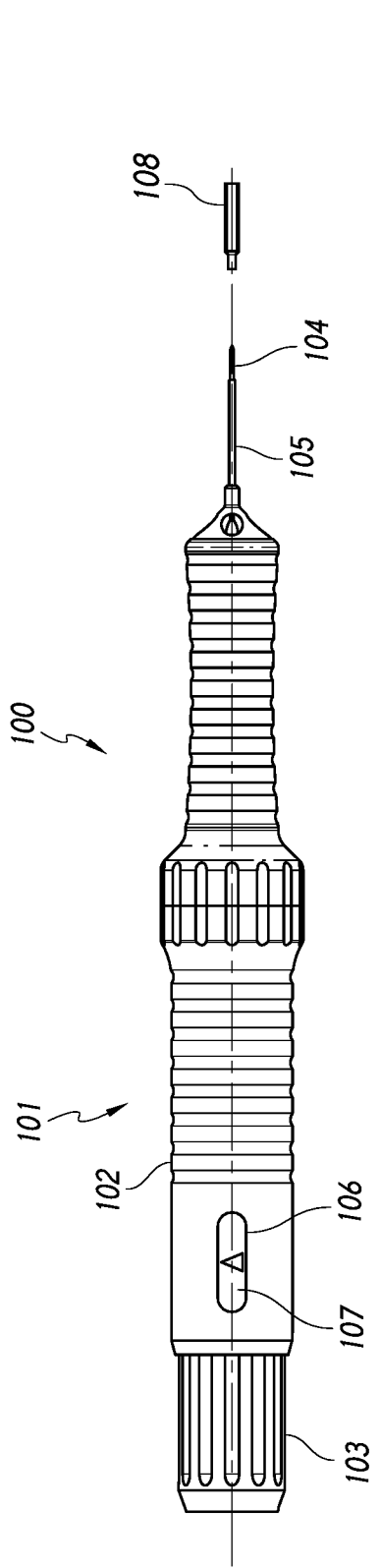
FIG. 1 is a schematic showing an embodiment of a shunt deployment device according to the invention.

Reference is now made to FIG. 1, which shows an embodiment of a shunt deployment device 100 according to the invention. While FIG. 1 shows a handheld manually operated shunt deployment device, it will be appreciated that devices of the invention may be coupled with robotic systems and may be completely or partially automated. As shown in FIG. 1, deployment device 100 includes a generally cylindrical body or housing 101; however, the body shape of housing 101 could be other than cylindrical. Housing 101 may have an ergonomical shape, allowing for comfortable grasping by an operator. Housing 101 is shown with optional grooves 102 to allow for easier gripping by a surgeon.

Housing 101 is shown having a larger proximal portion that tapers to a distal portion. The distal portion includes a hollow sleeve 105. The hollow sleeve 105 is configured for insertion into an eye and to extend into an anterior chamber of an eye. The hollow sleeve is visible within an anterior chamber of an eye. The sleeve 105 provides a visual preview for an operator as to placement of the proximal portion of the shunt within the anterior chamber of an eye. Additionally, the sleeve 105 provides a visual reference point that may be used by an operator to hold device 100 steady during the shunt deployment process, thereby assuring optimal longitudinal placement of the shunt within the eye.

The sleeve 105 may include an edge 131 at a distal end that provides resistance feedback to an operator upon insertion of the deployment device 100 within an eye 132 of a person during delivery of the shunt 115, as shown in FIGS. 10A-10E. Upon advancement of the device 100 across an anterior chamber 133 of the eye 132, the hollow sleeve 105 will eventually contact the sclera 134, providing resistance feedback to an operator that no further advancement of the device 100 is necessary. The edge 131 of the sleeve 105 prevents the shaft 104 from accidentally being pushed too far through the sclera 134. A temporary guard 108 is configured to fit around sleeve 105 and extend beyond an end of sleeve 105. The guard is used during shipping of the device and protects an operator from a distal end of a hollow shaft 104 that extends beyond the end of the sleeve 105. The guard is removed prior to use of the device.

Housing 101 is open at its proximal end, such that a portion of a deployment mechanism 103 may extend from the proximal end of the housing 101. A distal end of housing 101 is also open such that at least a portion of a hollow shaft 104 may extend through and beyond the distal end of the housing 101. Housing 101 further includes a slot 106 through which an operator, such as a surgeon, using the device 100 may view an indicator 107 on the deployment mechanism 103.

Housing 101 may be made of any material that is suitable for use in medical devices. For example, housing 101 may be made of a lightweight aluminum or a biocompatible plastic material. Examples of such suitable plastic materials include polycarbonate and other polymeric resins such as DELRIN and ULTEM. In certain embodiments, housing 101 is made of a material that may be autoclaved, and thus allow for housing 101 to be re-usable. Alternatively, device 100 may be sold as a one-time-use device, and thus the material of the housing does not need to be a material that is autoclavable.

Figure 2:
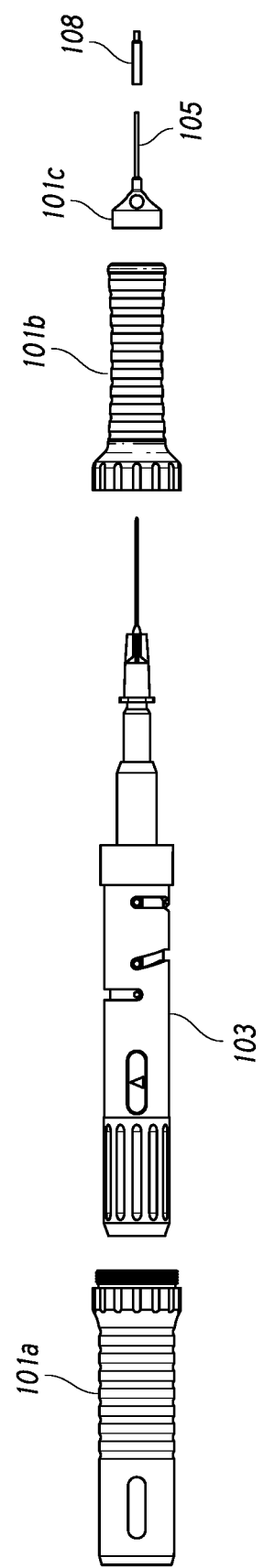
FIG. 2 shows an exploded view of the device shown in FIG. 1.

Housing 101 may be made of multiple components that connect together to form the housing. FIG. 2 shows an exploded view of deployment device 100. In this figure, housing 101, is shown having three components 101a, 101b, and 101c. The components are designed to screw together to form housing 101. FIG. 2 also shows deployment mechanism 103. The housing 101 is designed such that deployment mechanism 103 fits within assembled housing 101. Housing 101 is designed such that components of deployment mechanism 103 are movable within housing 101.

FIGS. 3A-3D show different enlarged views of the deployment mechanism 103. Deployment mechanism 103 may be made of any material that is suitable for use in medical devices. For example, deployment mechanism 103 may be made of a lightweight aluminum or a biocompatible plastic material. Examples of such suitable plastic materials include polycarbonate and other polymeric resins such as DELRIN and ULTEM. In certain embodiments, deployment mechanism 103 is made of a material that may be autoclaved, and thus allow for deployment mechanism 103 to be re-usable. Alternatively, device 100 may be sold as a one-time-use device, and thus the material of the deployment mechanism does not need to be a material that is autoclavable.

Deployment mechanism 103 includes a distal portion 109 and a proximal portion 110. The deployment mechanism 103 is configured such that distal portion 109 is movable within proximal portion 110. More particularly, distal portion 109 is capable of partially retracting to within proximal portion 110.

In this embodiment, the distal portion 109 is shown to taper to a connection with a hollow shaft 104. This embodiment is illustrated such that the connection between the hollow shaft 104 and the distal portion 109 of the deployment mechanism 103 occurs inside the housing 101. In other embodiments, the connection between hollow shaft 104 and the distal portion 109 of the deployment mechanism 103 may occur outside of the housing 101. Hollow shaft 104 may be removable from the distal portion 109 of the deployment mechanism 103. Alternatively, the hollow shaft 104 may be permanently coupled to the distal portion 109 of the deployment mechanism 103.

Figure 11:
FIG. 11 depicts a schematic of an exemplary intraocular shunt.

Generally, hollow shaft 104 is configured to hold an intraocular shunt 115. An exemplary intraocular shunt 115 is shown in FIG. 11. Other exemplary intraocular shunts are shown in Yu et al. (U.S. Patent Application No. 2008/0108933). Generally, in one embodiment, intraocular shunts are of a cylindrical shape and have an outside cylindrical wall and a hollow interior. The shunt may have an inner diameter of approximately 50 µm to approximately 250 µm, an outside diameter of approximately 190 µm to approximately 300 µm, and a length of approximately 0.5 mm to about 20 mm. Thus, hollow shaft 104 is configured to at least hold a shunt of such shape and such dimensions. However, hollow shaft 104 may be configured to hold shunts of different shapes and different dimensions than those described above, and the invention encompasses a shaft 104 that may be configured to hold any shaped or dimensioned intraocular shunt. In particular embodiments, the shaft has an inner diameter of approximately 200 µm to approximately 400 µm.

The shaft 104 may be any length. A usable length of the shaft may be anywhere from about 5 mm to about 40 mm, and is 15 mm in certain embodiments. In certain embodiments, the shaft is straight. In other embodiments, shaft is of a shape other than straight, for example a shaft having a bend along its length or a shaft having an arcuate portion. Exemplary shaped shafts are shown for example in Yu et al. (U.S. Patent Application No. 2008/0108933). In particular embodiments, the shaft includes a bend at a distal portion of the shaft. In other embodiments, a distal end of the shaft is beveled or is sharpened to a point.

The shaft 104 may hold the shunt at least partially within the hollow interior of the shaft 104. In other embodiments, the shunt is held completely within the hollow interior of the shaft 104. Alternatively, the hollow shaft may hold the shunt on an outer surface of the shaft 104. In particular embodiments, the shunt is held within the hollow interior of the shaft 104. In certain embodiments, the hollow shaft is a needle having a hollow interior. Needles that are configured to hold an intraocular shunt are commercially available from Terumo Medical Corp. (Elkington, Md.).

A proximal portion of the deployment mechanism includes optional grooves 116 to allow for easier gripping by an operator for easier rotation of the deployment mechanism, which will be discussed in more detail below. The proximal portion 110 of the deployment mechanism also includes at least one indicator that provides feedback to an operator as to the state of the deployment mechanism. The indicator may be any type of indicator known in the art, for example, a visual indicator, an audio indicator, or a tactile indicator. FIGS. 3A-3D show a deployment mechanism having two indicators, a ready indicator 111 and a deployed indicator 119. Ready indicator 111 provides feedback to an operator that the deployment mechanism is in a configuration for deployment of an intraocular shunt from the deployment device 100. The indicator 111 is shown in this embodiment as a green oval having a triangle within the oval. Deployed indicator 119 provides feedback to the operator that the deployment mechanism has been fully engaged and has deployed the shunt from the deployment device 100. The deployed indicator 119 is shown in this embodiment as a yellow oval having a black square within the oval. The indicators are located on the deployment mechanism such that when assembled, the indicators 111 and 119 may be seen through slot 106 in housing 101.

Figure 4A:
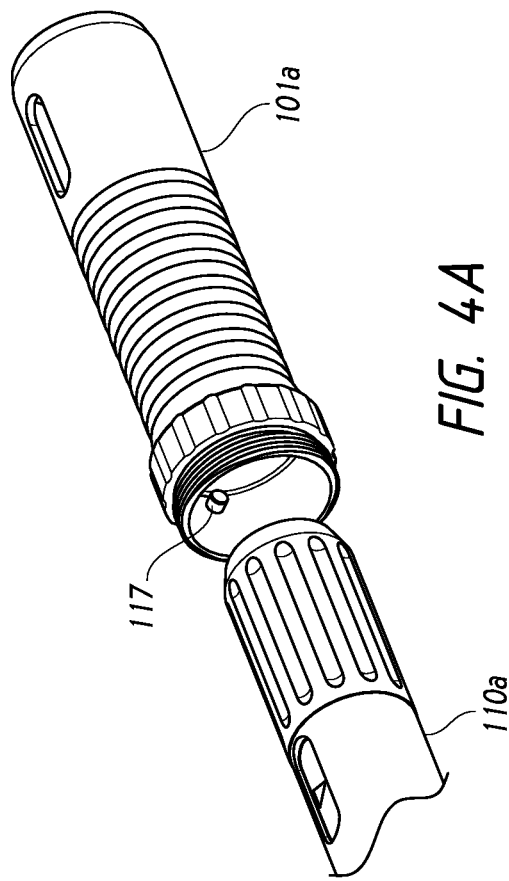
FIGS. 4A-4C are schematics showing interaction of the deployment mechanism with a portion of the housing of the deployment device.
Figure 4B:
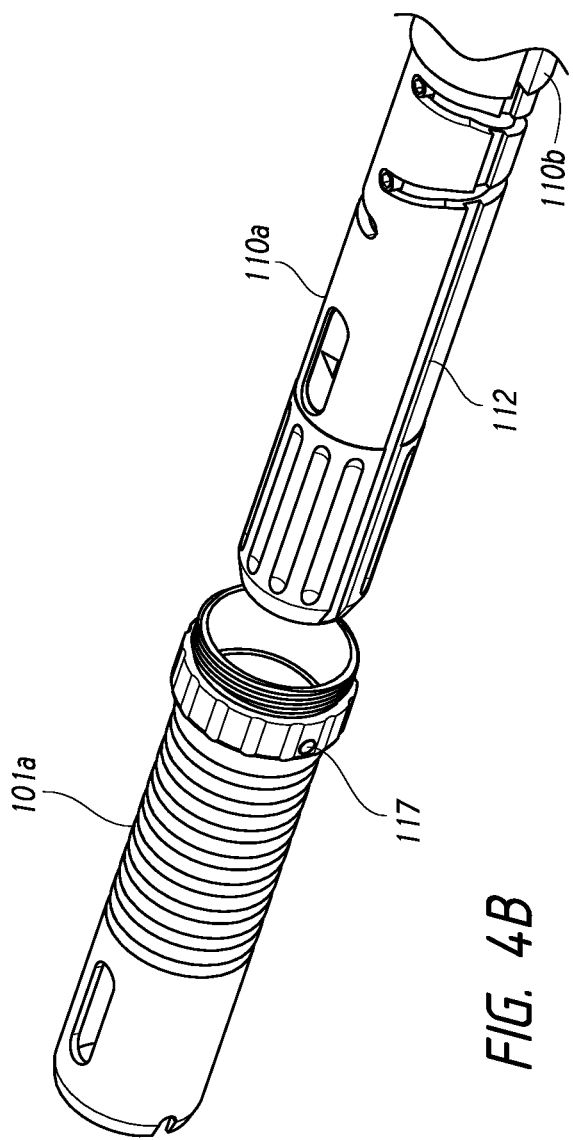
Figure 4C:
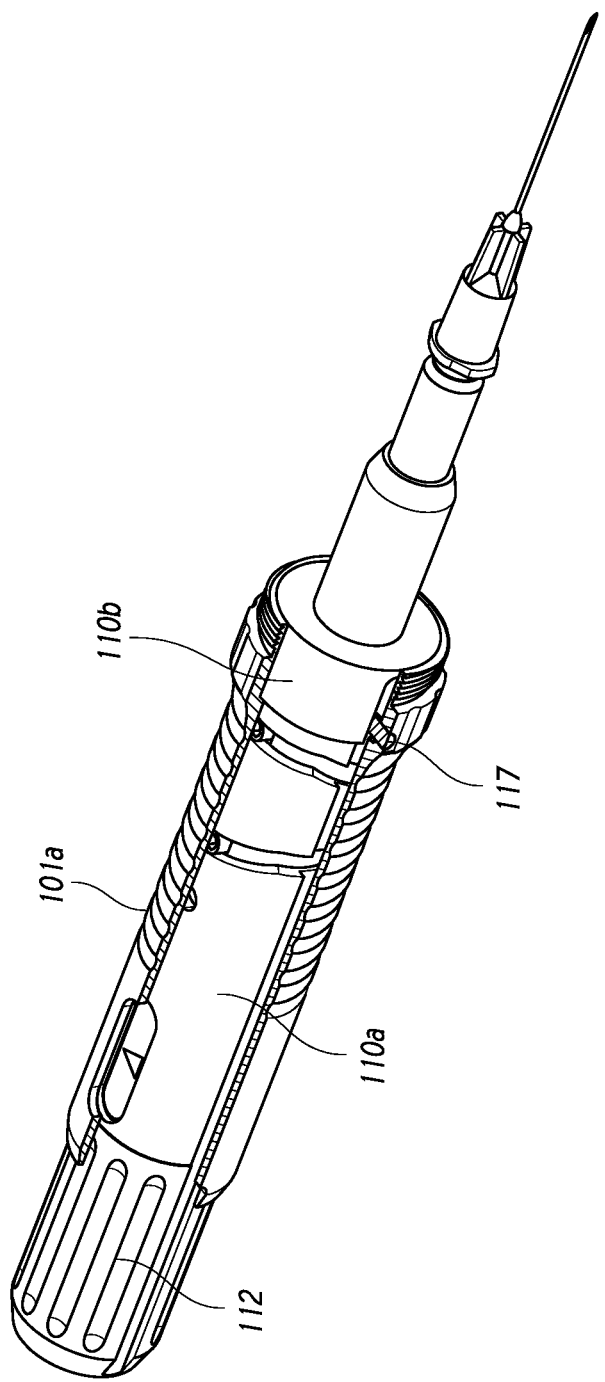

The proximal portion 110 includes a stationary portion 110b and a rotating portion 110a. The proximal portion 110 includes a channel 112 that runs part of the length of stationary portion 110b and the entire length of rotating portion 110a. The channel 112 is configured to interact with a protrusion 117 on an interior portion of housing component 101a (FIGS. 4A and 4B). During assembly, the protrusion 117 on housing component 101a is aligned with channel 112 on the stationary portion 110b and rotating portion 110a of the deployment mechanism 103. The proximal portion 110 of deployment mechanism 103 is slid within housing component 101a until the protrusion 117 sits within stationary portion 110b (FIG. 4C). Assembled, the protrusion 117 interacts with the stationary portion 110b of the deployment mechanism 103 and prevents rotation of stationary portion 110b. In this configuration, rotating portion 110a is free to rotate within housing component 101a.

Referring back to FIGS. 3A-3D, the rotating portion 110a of proximal portion 110 of deployment mechanism 103 also includes channels 113a, 113b, and 113c. Channel 113a includes a first portion 113a1 that is straight and runs perpendicular to the length of the rotating portion 110a, and a second portion 113a2 that runs diagonally along the length of rotating portion 110a, downwardly toward a proximal end of the deployment mechanism 103. Channel 113b includes a first portion 113b1 that runs diagonally along the length of the rotating portion 110a, downwardly toward a distal end of the deployment mechanism 103, and a second portion that is straight and runs perpendicular to the length of the rotating portion 110a. The point at which first portion 113a1 transitions to second portion 113a2 along channel 113a, is the same as the point at which first portion 113b1 transitions to second portion 113b2 along channel 113b. Channel 113c is straight and runs perpendicular to the length of the rotating portion 110a. Within each of channels 113a, 113b, and 113c, sit members 114a, 114b, and 114c respectively. Members 114a, 114b, and 114c are movable within channels 113a, 113b, and 113c. Members 114a, 114b, and 114c also act as stoppers that limit movement of rotating portion 110a, which thereby limits axial movement of the shaft 104.

Figure 5:
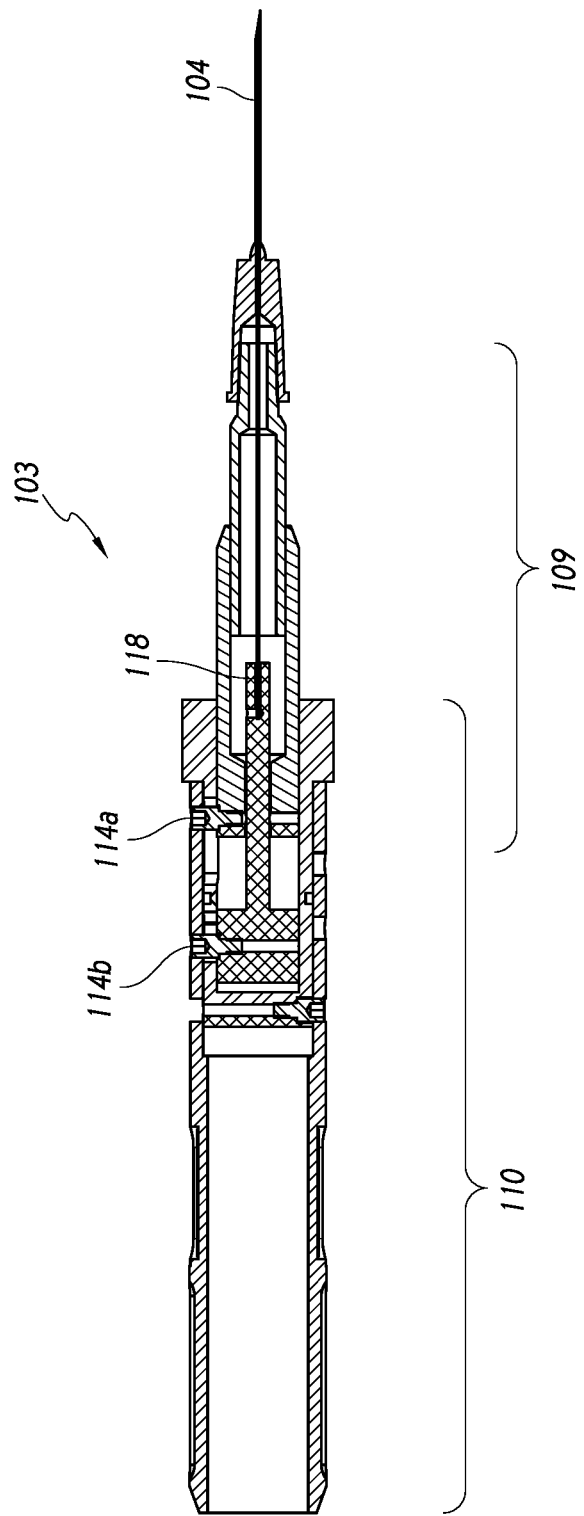
FIG. 5 shows a cross sectional view of the deployment mechanism of the deployment device.

FIG. 5 shows a cross-sectional view of deployment mechanism 103. Member 114a is connected to the distal portion 109 of the deployment mechanism 103. Movement of member 114a results in retraction of the distal portion 109 of the deployment mechanism 103 to within the proximal portion 110 of the deployment mechanism 103. Member 114b is connected to a pusher component 118. The pusher component 118 extends through the distal portion 109 of the deployment mechanism 103 and extends into a portion of hollow shaft 104. The pusher component is involved in deployment of a shunt from the hollow shaft 104. An exemplary pusher component is a plunger. Movement of member 114b engages pusher 118 and results in pusher 118 advancing within hollow shaft 104.

Figure 6A:
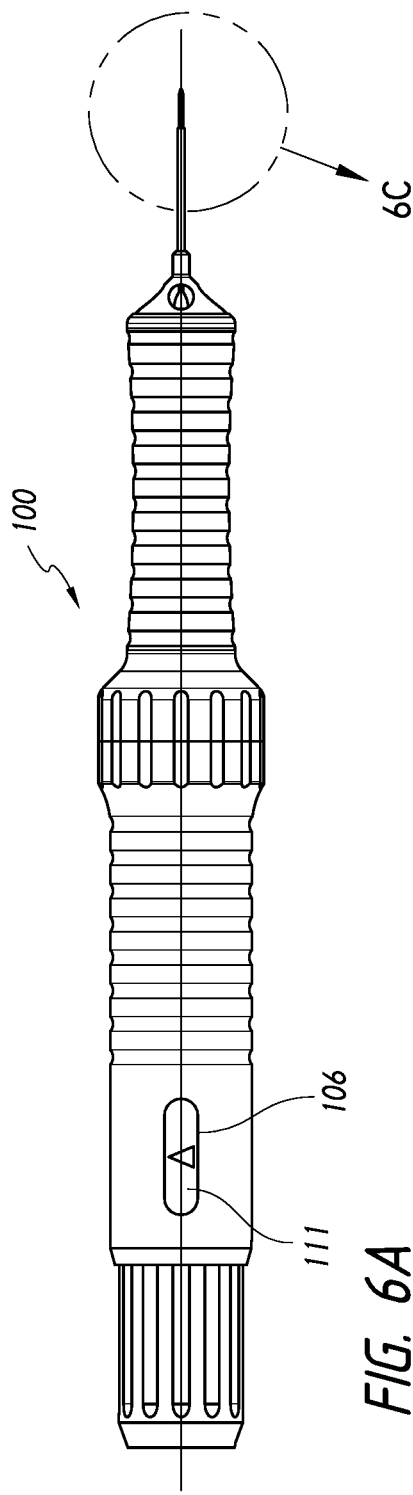
FIGS. 6A and 6B show schematics of the deployment mechanism in a pre-deployment configuration.

Reference is now made to FIGS. 6A-8D, which accompany the following discussion regarding deployment of a shunt 115 from deployment device 100. FIG. 6A shows deployment device 100 in a pre-deployment configuration. In this configuration, shunt 115 is loaded within hollow shaft 104 (FIG. 6C). As shown in FIG. 6C, shunt 115 is only partially within shaft 104, such that a portion of the shunt is exposed. However, the shunt 115 does not extend beyond the end of the shaft 104. In other embodiments, the shunt 115 is completely disposed within hollow shaft 104. The shunt 115 is loaded into hollow shaft 104 such that the shunt abuts pusher component 118 within hollow shaft 104. A distal end of shaft 104 is beveled to assist in piercing tissue of the eye.

Figure 6B:
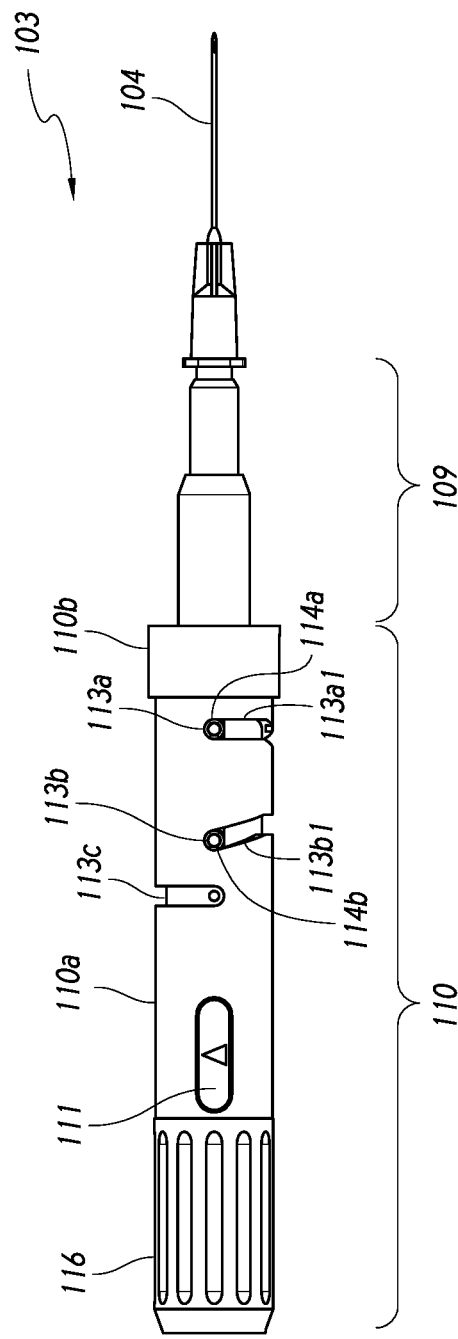
Figure 6C:
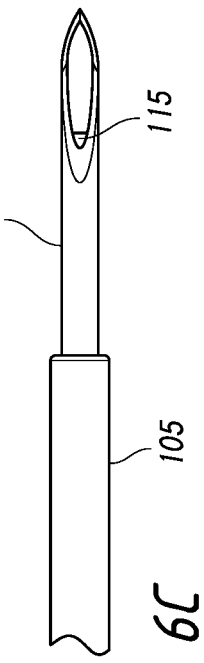
FIG. 6C shows an enlarged view of the distal portion of the deployment device of FIG. 6A. This figure shows an intraocular shunt loaded within a hollow shaft of the deployment device.

Additionally, in the pre-deployment configuration, a portion of the shaft 104 extends beyond the sleeve 105 (FIG. 6C). The deployment mechanism is configured such that member 114a abuts a distal end of the first portion 113a1 of channel 113a, and member 114b abut a proximal end of the first portion 113b1 of channel 113b (FIG. 6B). In this configuration, the ready indicator 111 is visible through slot 106 of the housing 101, providing feedback to an operator that the deployment mechanism is in a configuration for deployment of an intraocular shunt from the deployment device 100 (FIG. 6A). In this configuration, the device 100 is ready for insertion into an eye (insertion configuration or pre-deployment configuration). Methods for inserting and implanting shunts are discussed in further detail below.

Once the device has been inserted into the eye and advanced to a location to where the shunt will be deployed, the shunt 115 may be deployed from the device 100. The deployment mechanism 103 is a two-stage system. The first stage is engagement of the pusher component 118 and the second stage is retraction of the distal portion 109 to within the proximal portion 110 of the deployment mechanism 103. Rotation of the rotating portion 110a of the proximal portion 110 of the deployment mechanism 103 sequentially engages the pusher component and then the retraction component.

In the first stage of shunt deployment, the pusher component is engaged and the pusher partially deploys the shunt from the deployment device. During the first stage, rotating portion 110a of the proximal portion 110 of the deployment mechanism 103 is rotated, resulting in movement of members 114a and 114b along first portions 113a1 and 113b1 in channels 113a and 113b. Since the first portion 113a1 of channel 113a is straight and runs perpendicular to the length of the rotating portion 110a, rotation of rotating portion 110a does not cause axial movement of member 114a. Without axial movement of member 114a, there is no retraction of the distal portion 109 to within the proximal portion 110 of the deployment mechanism 103. Since the first portion 113b1 of channel 113b runs diagonally along the length of the rotating portion 110a, upwardly toward a distal end of the deployment mechanism 103, rotation of rotating portion 110a causes axial movement of member 114b toward a distal end of the device. Axial movement of member 114b toward a distal end of the device results in forward advancement of the pusher component 118 within the hollow shaft 104. Such movement of pusher component 118 results in partially deployment of the shunt 115 from the shaft 104.

Figure 7A:
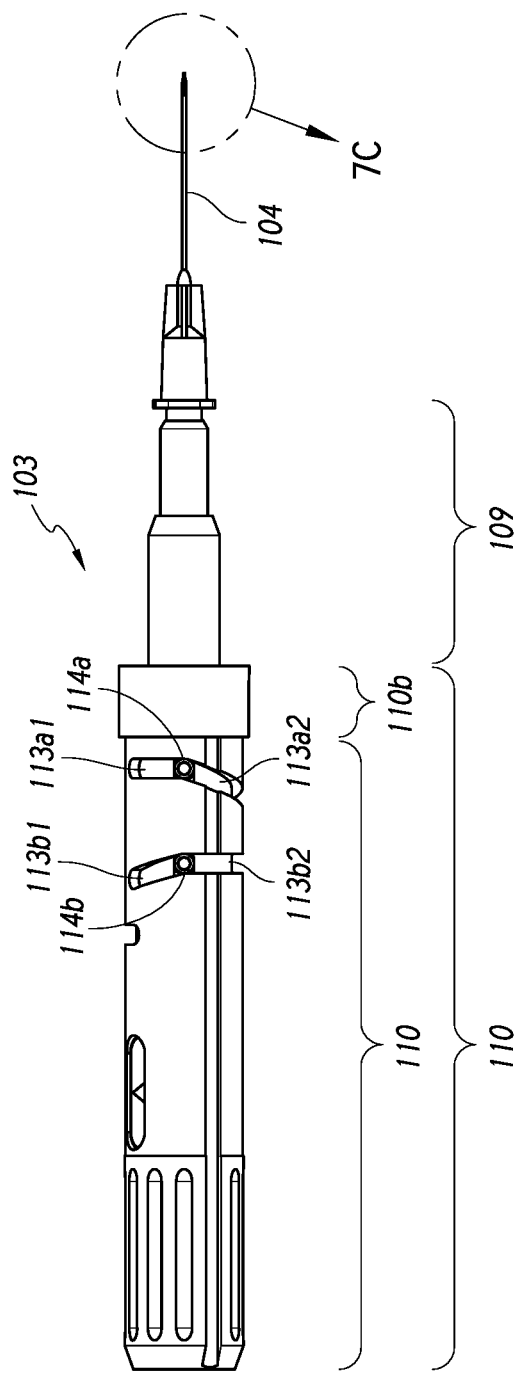
FIGS. 7A and 7B show schematics of the deployment mechanism at the end of the first stage of deployment of the shunt from the deployment device.
Figure 7B:
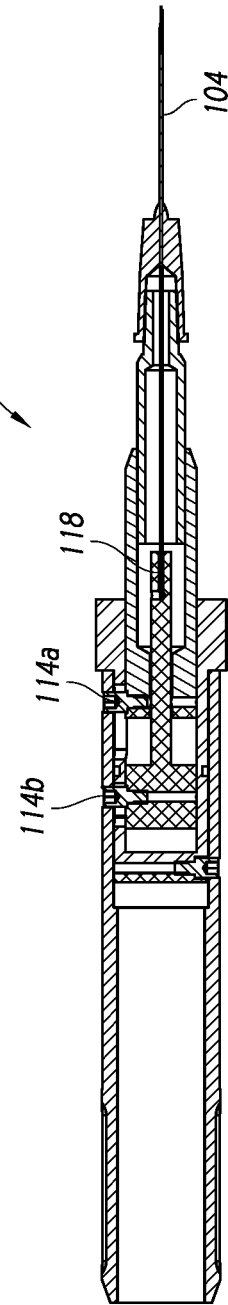
Figure 7C:
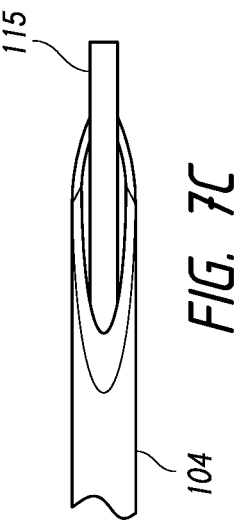
FIG. 7C shows an enlarged view of the distal portion of the deployment device of FIG. 7A. This figure shows an intraocular shunt partially deployed from within a hollow shaft of the deployment device.

FIGS. 7A-7C show schematics of the deployment mechanism at the end of the first stage of deployment of the shunt from the deployment device. As is shown FIG. 7A, members 114a and 114b have finished traversing along first portions 113a1 and 113b1 of channels 113a and 113b. Additionally, pusher component 118 has advanced within hollow shaft 104 (FIG. 7B), and shunt 115 has been partially deployed from the hollow shaft 104 (FIG. 7C). As is shown in these figures, a portion of the shunt 115 extends beyond an end of the shaft 104.

Figure 8C:
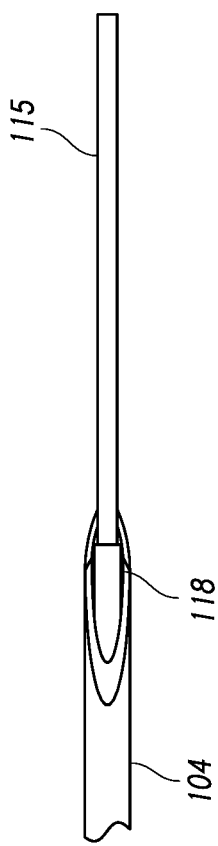
FIG. 8C shows an enlarged view of the distal portion of the deployment device after retraction of the shaft with the pusher abutting the shunt.

In the second stage of shunt deployment, the retraction component is engaged and the distal portion of the deployment mechanism is retracted to within the proximal portion of the deployment mechanism, thereby completing deployment of the shunt from the deployment device. During the second stage, rotating portion 110a of the proximal portion 110 of the deployment mechanism 103 is further rotated, resulting in movement of members 114a and 114b along second portions 113a2 and 113b2 in channels 113a and 113b. Since the second portion 113b2 of channel 113b is straight and runs perpendicular to the length of the rotating portion 110a, rotation of rotating portion 110a does not cause axial movement of member 114b. Without axial movement of member 114b, there is no further advancement of pusher 118. Since the second portion 113a2 of channel 113a runs diagonally along the length of the rotating portion 110a, downwardly toward a proximal end of the deployment mechanism 103, rotation of rotating portion 110a causes axial movement of member 114a toward a proximal end of the device. Axial movement of member 114a toward a proximal end of the device results in retraction of the distal portion 109 to within the proximal portion 110 of the deployment mechanism 103. Retraction of the distal portion 109, results in retraction of the hollow shaft 104. Since the shunt 115 abuts the pusher component 118, the shunt remains stationary as the hollow shaft 104 retracts from around the shunt 115 (FIG. 8C). The shaft 104 retracts almost completely to within the sleeve 105. During both stages of the deployment process, the sleeve 105 remains stationary and in a fixed position.

Figure 8D:
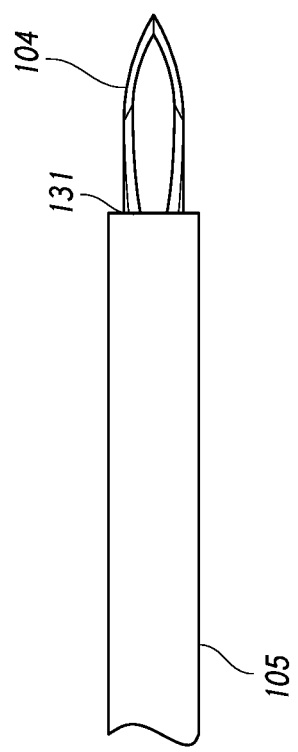
FIG. 8D shows an enlarged view of the distal portion of the deployment device after deployment of the shunt.

FIG. 8A-8D show schematics of the device 100 after deployment of the shunt 115 from the device 100. FIG. 8B shows a schematic of the deployment mechanism at the end of the second stage of deployment of the shunt from the deployment device. As is shown in FIG. 8B, members 114a and 114b have finished traversing along second portions 113a2 and 113b2 of channels 113a and 113b. Additionally, distal portion 109 has retracted to within proximal portion 110, thus resulting in retraction of the hollow shaft 104 to within the sleeve 105. FIG. 8D shows an enlarged view of the proximal portion of the deployment device after deployment of the shunt. This figure shows that the hollow shaft 104 is not fully retracted to within the sleeve 105 of the deployment device 100. However, in certain embodiments, the shaft 104 may completely retract to within the sleeve 105.

Referring to FIG. 8A, in the post-deployment configuration, the deployed indicator 119 is visible through slot 106 of the housing 101, providing feedback to the operator that the deployment mechanism has been fully engaged and that the shunt 115 has been deployed from the deployment device 100.

Any of a variety of methods known in the art may be used to insert devices of the invention into an eye. In certain embodiments, devices of the invention may be inserted into the eye using an ab externo approach (entering through the conjunctiva) or an ab interno approach (entering through the cornea).

In certain embodiments, devices of the invention are inserted into the eye using an ab interno approach. Ab interno approaches for implanting an intraocular shunt are shown for example in Yu et al. (U.S. Pat. No. 6,544,249 and U.S. Patent Application No. 2008/0108933) and Prywes (U.S. Pat. No. 6,007,511), the content of each of which is incorporated by reference herein in its entirety.

Devices of the invention may be inserted into the eye to deploy shunts that create fluid drainage passageways from the anterior chamber of the eye to various drainage structures of the eye. Exemplary drainage structures include Schlemm's canal, the subconjunctival space, the episcleral vein, the suprachoroidal space, or the intra-Tenon's space. In certain embodiments, fluid is drained to the subarachnoid space.

In particular embodiments, devices of the invention are inserted into the eye to deploy shunts that create fluid drainage passageways from the anterior chamber to the intra-Tenon's space. Within an eye, there is a membrane known as the conjunctiva, and the region below the conjunctiva is known as the subconjunctival space. Within the subconjunctival space is a membrane known as Tenon's capsule. Below Tenon's capsule there are Tenon's adhesions that connect the Tenon's capsule to the sclera. The space between Tenon's capsule and the sclera where the Tenon's adhesions connect the Tenon's capsule to the sclera is known as the intra-Tenon's space.

Figure 9A:
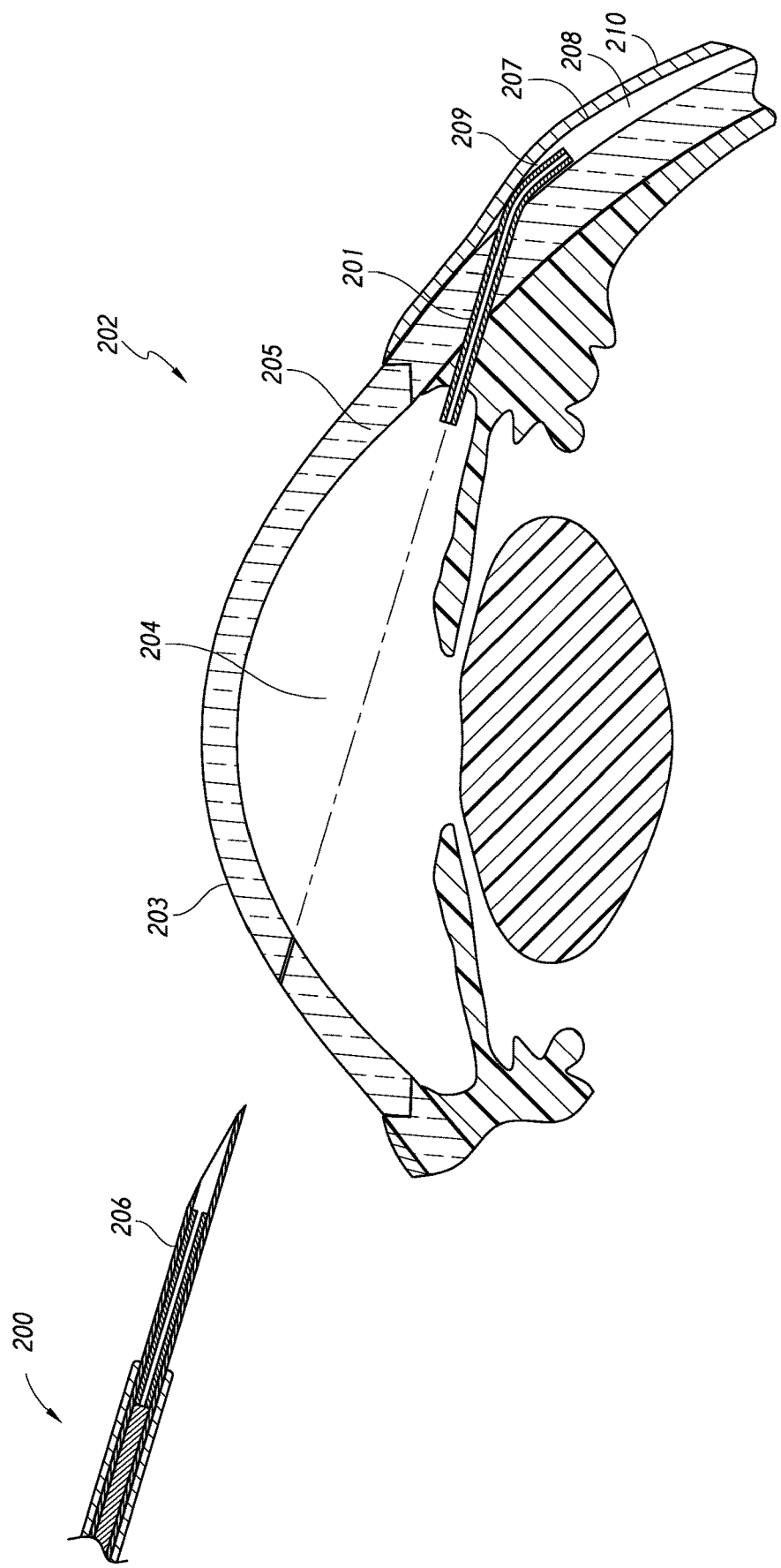
FIGS. 9A and 9B show an intraocular shunt deployed within the eye. A proximal portion of the shunt resides in the anterior chamber and a distal portion of the shunt resides within the intra-Tenon's space. A middle portion of the shunt resides in the sclera.
Figure 9B:
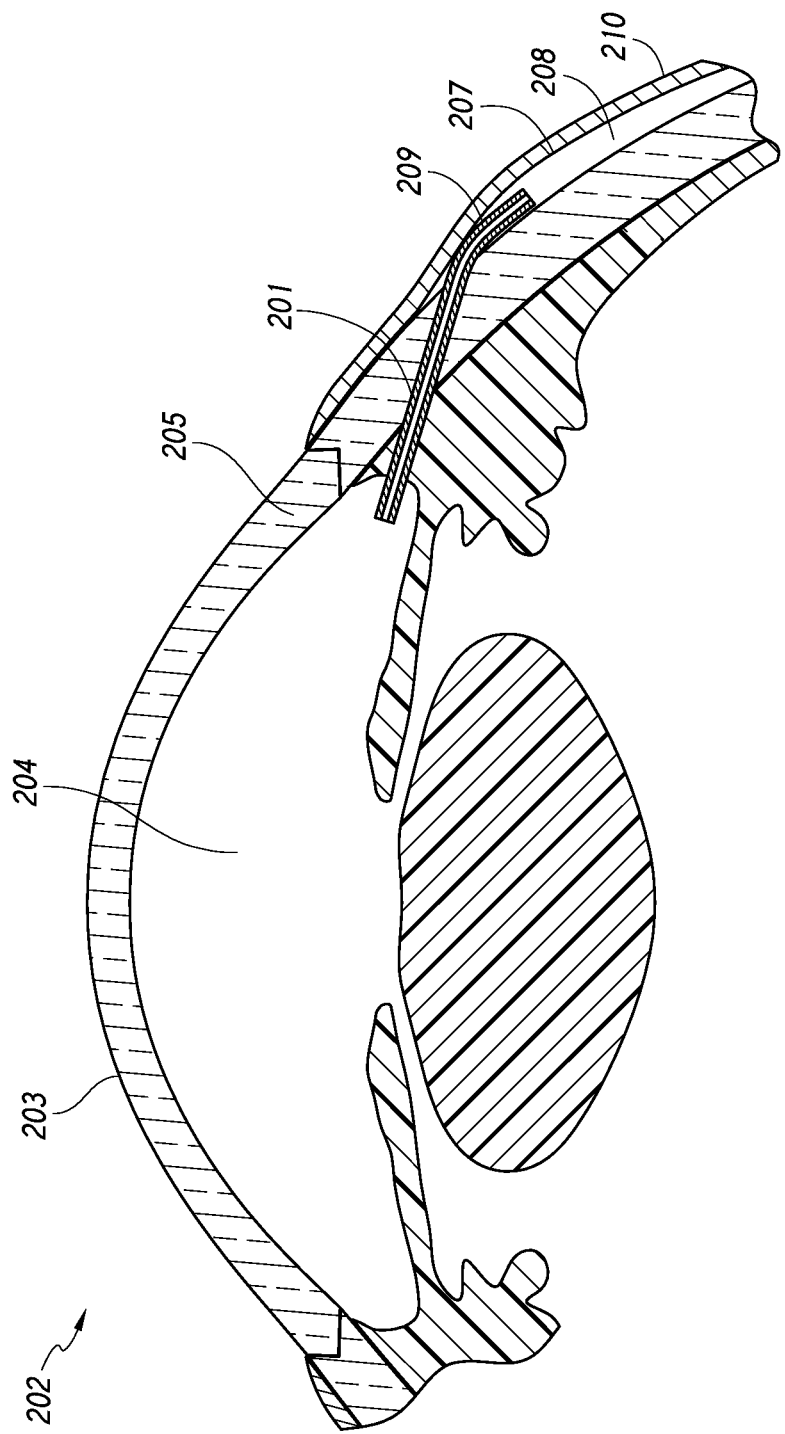
Figure 10A:
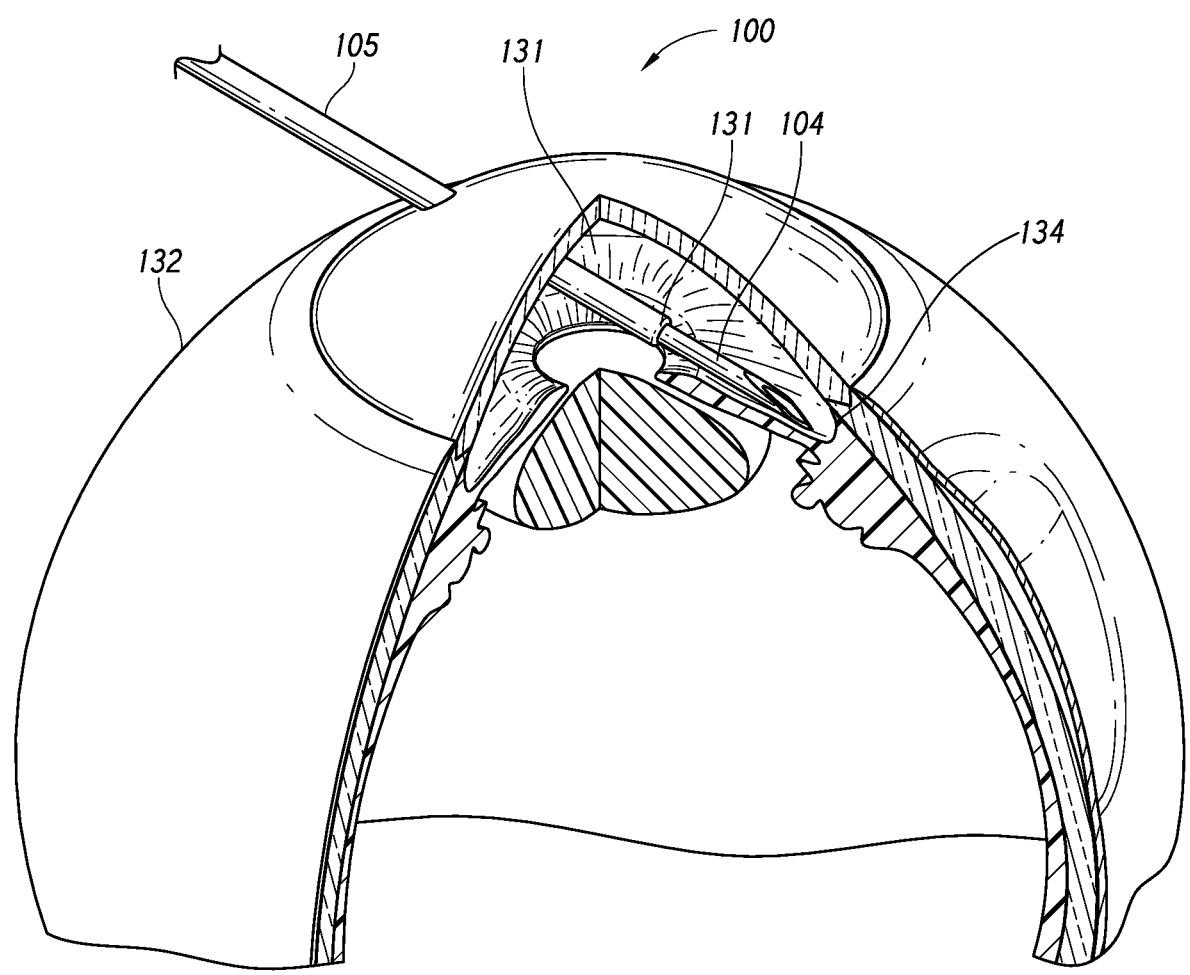
FIGS. 10A-10E show an intraocular shunt being deployed within the eye, according to another embodiment.
Figure 10B:
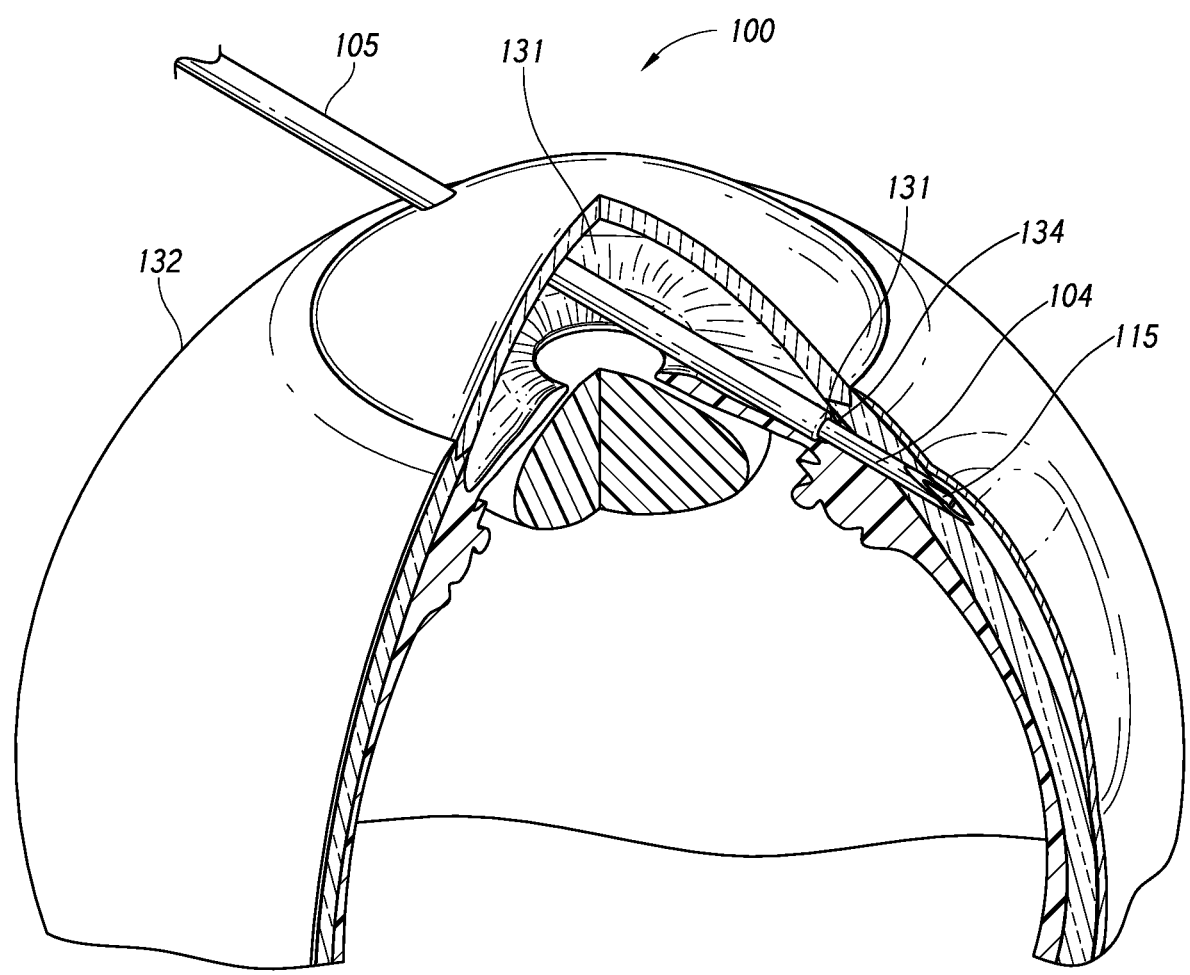
Figure 10C:
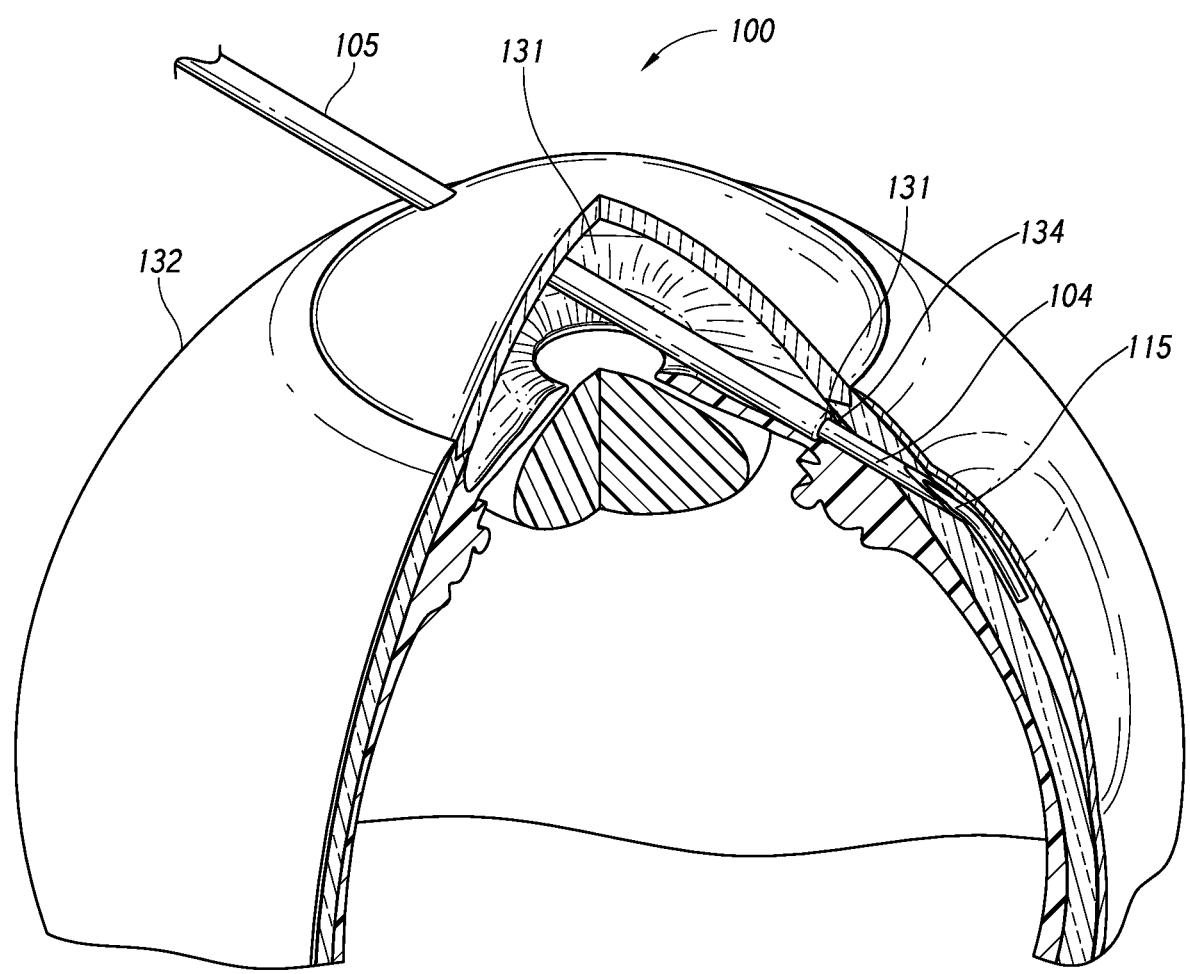
Figure 10D:
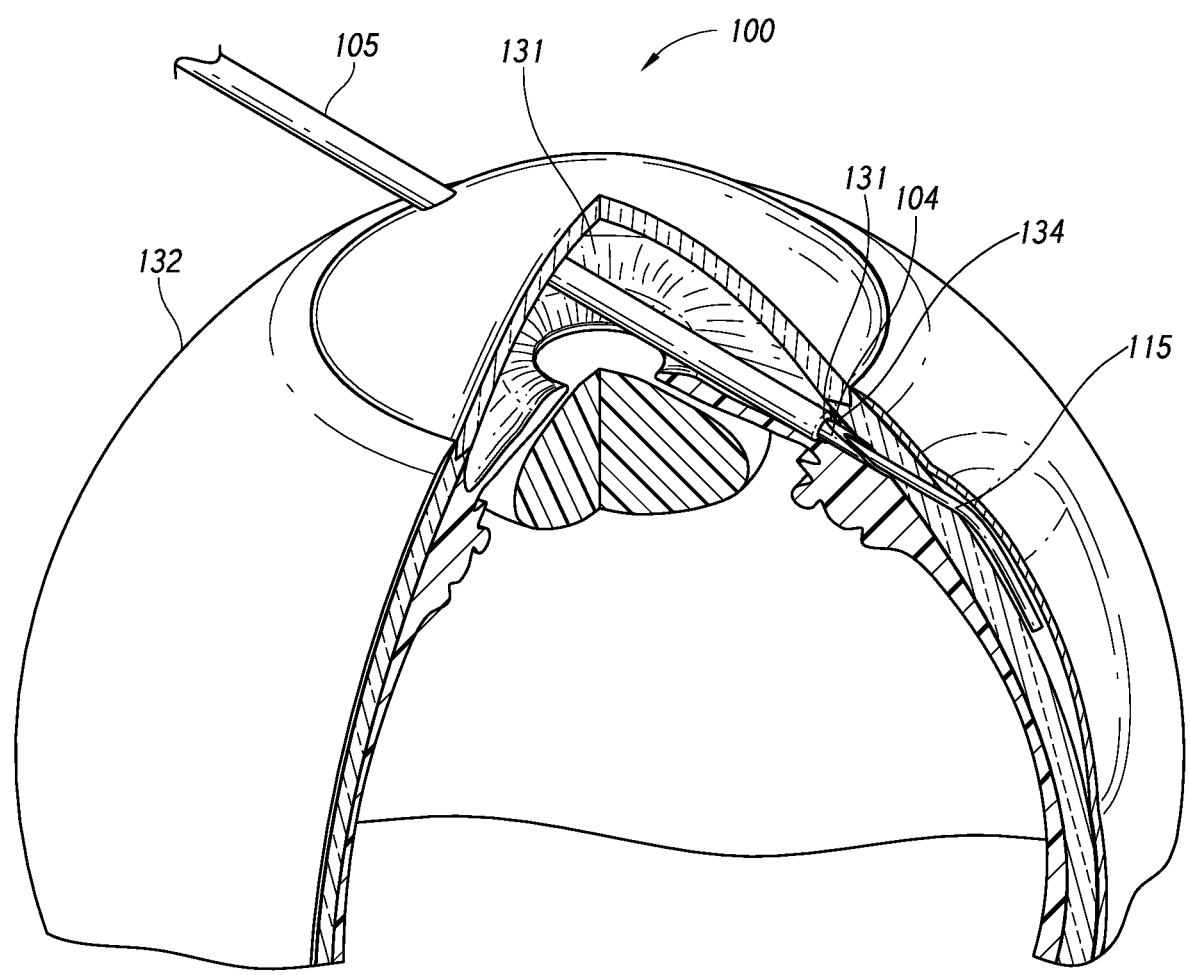
Figure 10E:
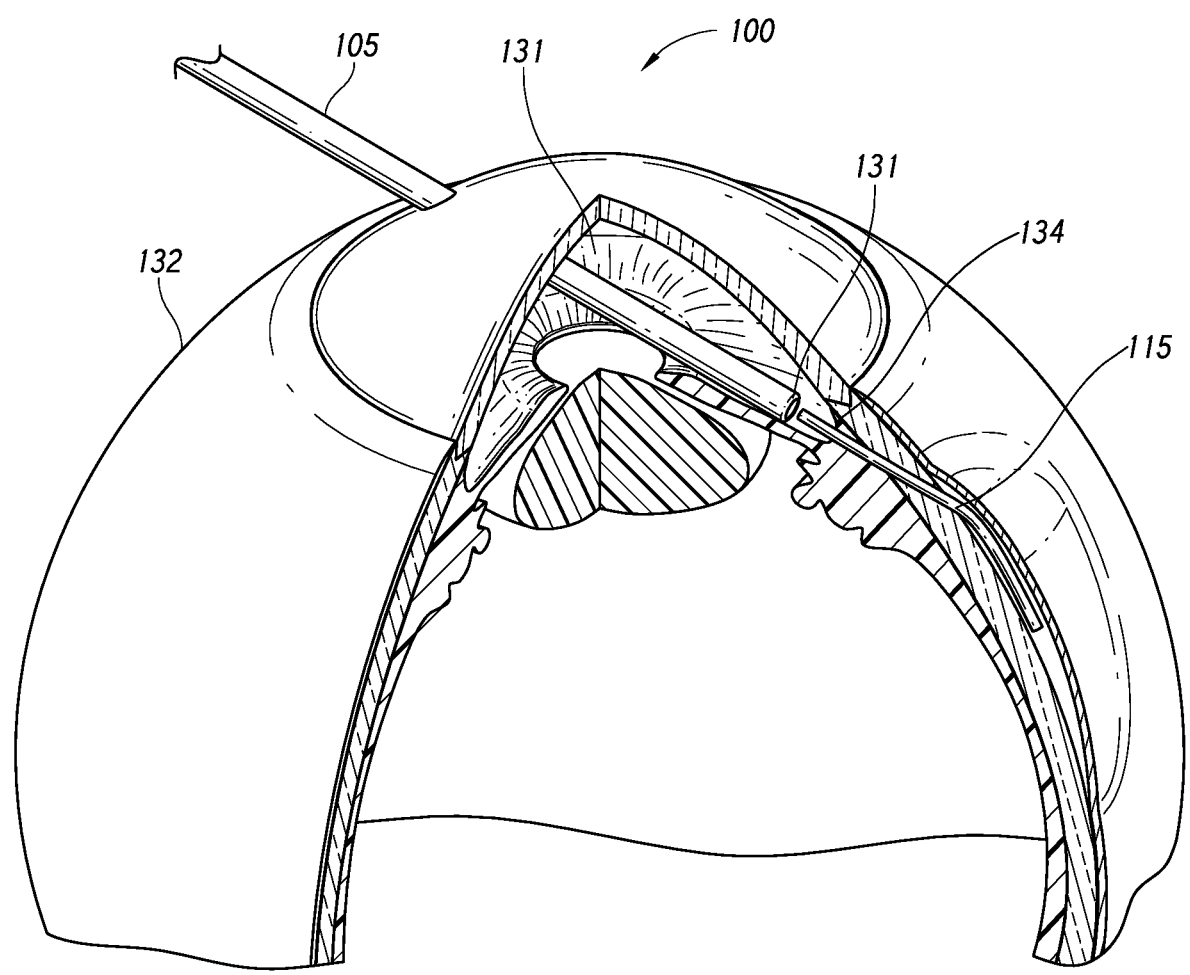

FIGS. 9A and 9B show an intraocular shunt placed into the eye using devices of the invention such that the shunt forms a passage for fluid drainage from the anterior chamber to the intra-Tenon's space. To place the shunt within the eye, a surgical intervention to implant the shunt is performed that involves inserting into the eye 202 a deployment device 200 that holds an intraocular shunt 201, and deploying at least a portion of the shunt 201 within intra-Tenon's space 208, within the subconjunctival space 209 and below the conjunctiva 210. In certain embodiments, a hollow shaft 206 of a deployment device 200 holding the shunt 201 enters the eye 202 through the cornea 203 (ab interno approach). The shaft 206 is advanced across the anterior chamber 204 (as depicted by the broken line) in what is referred to as a transpupil implant insertion. The shaft 206 is advanced through the sclera 205 until a distal portion of the shaft 206 is in proximity to Tenon's capsule 207.

Once a distal portion of the hollow shaft 206 is within the intra-Tenon's space 208, the shunt 201 is then deployed from the shaft 206 of the deployment device 200, producing a conduit between the anterior chamber 204 and the intra-Tenon's space 208 to allow aqueous humor to drain from the anterior chamber 204 (see FIGS. 9A and 9B).

Combinations of Embodiments

As will be appreciated by one skilled in the art, individual features of the invention may be used separately or in any combination. Particularly, it is contemplated that one or more features of the individually described above embodiments may be combined into a single shunt.

Incorporation by Reference

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A method for deploying an intraocular shunt within an eye, the method comprising:
providing a device comprising a hollow shaft configured to hold an intraocular shunt and a sleeve providing a visual preview component disposed along the shaft;
inserting the device into a cornea of the eye;
advancing the shaft into an anterior chamber angle of the eye; and
while maintaining the visual preview component at a substantially fixed position within the anterior chamber, advancing the shunt from the device for assuring optimal longitudinal placement within the eye.

2. The method of claim 1, wherein the advancing the device comprises advancing the shaft into the anterior chamber angle until the visual preview component is positioned at the substantially fixed position, spaced apart from the anterior chamber angle for releasing a proximal end of the shunt at the substantially fixed position after the shunt is advanced from the device.

3. The method of claim 1, wherein in the substantially fixed position, the visual preview component is spaced apart from anterior chamber angle tissue.

4. The method of claim 1, wherein the advancing the device comprises advancing the device until the visual preview component contacts the anterior chamber angle to provide resistance against further advancement of the device.

5. The method of claim 4, wherein the visual preview component comprises a sleeve, the shaft being disposed within the sleeve, and wherein the advancing comprises advancing the device until a distal edge of the sleeve contacts the anterior chamber angle.

6. The method of claim 1, wherein the advancing the shunt is performed while the visual preview component is spaced apart from the anterior chamber angle at the fixed position.

7. The method of claim 1, wherein the device comprises a deployment mechanism at least partially disposed within a housing thereof, and wherein rotation of the deployment mechanism results in axial movement of the shaft relative to the shunt to advance the shunt relative to the shaft, the method further comprising rotating the deployment mechanism to advance the shunt from the device and into the eye.

8. The method of claim 7, wherein the device comprises a sleeve, the shaft disposed within the sleeve, and wherein the rotating causes proximal axial movement of a distal end of the shaft into the sleeve.

9. The method of claim 1, wherein the advancing comprises forming a flow path from an anterior chamber of the eye to an area of lower pressure.

10. The method of claim 9, wherein the area of lower pressure is superficial to an inner surface of sclera.

11. The method of claim 9, wherein the area of lower pressure is selected from the group consisting of: intra-Tenon's space, a subconjunctival space, an episcleral vein, a suprachoroidal space, and Schlemm's canal.

12. A method for deploying an intraocular shunt within an eye, the method comprising:
inserting a hollow shaft of a device through a cornea into an anterior chamber angle of the eye;
positioning a sleeve providing a visual preview component of the device within the eye at a position spaced apart from the anterior chamber angle; and
while maintaining the position of the visual preview component, advancing the shunt from the device for assuring optimal longitudinal placement within the eye.

13. The method of claim 12, further comprising releasing a proximal end of the shunt at the desired location after the shunt is advanced from the device.

14. The method of claim 12, wherein the advancing the device comprises advancing the device until the visual preview component contacts the anterior chamber angle to provide resistance against further advancement of the device.

15. The method of claim 14, wherein the visual preview component comprises a sleeve, the shaft being disposed within the sleeve, and wherein the advancing comprises advancing the device until a distal edge of the sleeve contacts the anterior chamber angle.

16. The method of claim 12, wherein the advancing the device comprises forming a flow path from an anterior chamber of the eye to an area of lower pressure selected from the group consisting of: intra-Tenon's space, a subconjunctival space, an episcleral vein, a suprachoroidal space, and Schlemm's canal.

17. The method of claim 12, wherein the advancing the shunt is performed while the visual preview component is spaced apart from the anterior chamber angle at the fixed position.

18. The method of claim 12, wherein the device comprises a deployment mechanism at least partially disposed within a housing thereof, and wherein rotation of the deployment mechanism results in axial movement of the shaft relative to the shunt to advance the shunt relative to the shaft, the method further comprising rotating the deployment mechanism to advance the shunt from the device and into the eye.

19. The method of claim 18, wherein the device comprises a sleeve, the shaft disposed within the sleeve, and wherein the rotating causes proximal axial movement of a distal end of the shaft into the sleeve.

* * * * *